US010214479B2

(12) United States Patent
Kosinski et al.

(10) Patent No.: US 10,214,479 B2
(45) Date of Patent: *Feb. 26, 2019

(54) SYNTHESIS OF AND COMPOSITIONS CONTAINING DIAMINOACETALS AND DIAMINOKETALS

(71) Applicant: Connora Technologies, Inc., Hayward, CA (US)

(72) Inventors: Szymon Kosinski, Hayward, CA (US); Stefan J. Pastine, San Francisco, CA (US)

(73) Assignee: Connora Technologies, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,521

(22) Filed: Jan. 3, 2017

(65) Prior Publication Data
US 2017/0114002 A1 Apr. 27, 2017

Related U.S. Application Data

(63) Continuation of application No. 14/406,095, filed as application No. PCT/US2013/044346 on Jun. 5, 2013.

(60) Provisional application No. 61/655,794, filed on Jun. 5, 2012.

(51) Int. Cl.
C07C 213/02 (2006.01)

(52) U.S. Cl.
CPC ........... C07C 213/02 (2013.01); Y02P 20/582 (2015.11); Y02P 20/584 (2015.11)

(58) Field of Classification Search
None
See application file for complete search history.

(56) References Cited

U.S. PATENT DOCUMENTS

| 2,363,464 | A | 11/1944 | Murray et al. |
| 2,409,675 | A * | 10/1946 | Gresham ............... B01J 29/70 558/448 |
| 2,425,628 | A | 8/1947 | Donald et al. |
| 3,293,298 | A | 12/1966 | Szabo |
| 3,462,393 | A | 8/1969 | Legler |
| 3,501,528 | A | 3/1970 | Ott |
| 3,558,709 | A | 1/1971 | Gunter |
| 3,786,029 | A | 1/1974 | Bechara |
| 3,879,465 | A | 4/1975 | Bechara et al. |
| 4,003,933 | A | 1/1977 | Drake |
| 4,136,092 | A | 1/1979 | Jackie et al. |
| 4,177,173 | A | 12/1979 | Carr |
| 4,235,821 | A | 11/1980 | Butte, Jr. et al. |
| 4,252,936 | A | 2/1981 | Rinde et al. |
| 4,313,004 | A | 1/1982 | Kluger et al. |
| 4,328,331 | A | 5/1982 | Chen et al. |
| 4,495,317 | A | 1/1985 | Albers |
| 4,581,423 | A | 4/1986 | Speranza et al. |
| 4,820,743 | A | 4/1989 | Ishikawa et al. |
| 4,929,661 | A | 5/1990 | Noomen et al. |
| 5,191,015 | A | 3/1993 | Sheppard et al. |
| 5,298,618 | A | 3/1994 | Speranza et al. |
| 5,310,789 | A | 5/1994 | Furihata et al. |
| 5,338,568 | A | 8/1994 | Lohnes et al. |
| 5,891,367 | A | 4/1999 | Basheer et al. |
| 5,932,682 | A | 8/1999 | Buchwalter et al. |
| 6,790,995 | B2 | 9/2004 | Pfeffinger et al. |
| 8,785,694 | B2 * | 7/2014 | Pastine ................. C07C 213/02 564/491 |
| 9,080,004 | B2 | 7/2015 | Abrami et al. |
| 2002/0045057 | A1 | 4/2002 | Guritza |
| 2005/0234216 | A1 | 10/2005 | Klein et al. |
| 2006/0014924 | A1 | 1/2006 | Hanley et al. |
| 2008/0207655 | A1 | 8/2008 | Dillon et al. |
| 2009/0030125 | A1 | 1/2009 | Vedage et al. |
| 2009/0048370 | A1 | 2/2009 | Lutz et al. |
| 2009/0137777 | A1 | 5/2009 | Iwashima et al. |
| 2009/0192265 | A1 | 7/2009 | Hasegawa et al. |
| 2010/0184890 | A1 | 7/2010 | Constantinescu et al. |
| 2011/0048637 | A1 | 3/2011 | Kohli |
| 2011/0244245 | A1 | 10/2011 | Elgimiabi |
| 2012/0012505 | A1 | 1/2012 | Compton |
| 2012/0301726 | A1 | 11/2012 | Staunton et al. |
| 2013/0245204 | A1 | 9/2013 | Pastine et al. |
| 2014/0221510 | A1 | 8/2014 | Liang et al. |
| 2014/0357802 | A1 | 12/2014 | Aou et al. |
| 2015/0050659 | A1 | 2/2015 | Sebo et al. |
| 2016/0229949 | A1 | 8/2016 | Qin et al. |

FOREIGN PATENT DOCUMENTS

| DE | 1125171 B | 3/1962 |
| GB | 846377 A | 8/1960 |
| JP | 1225635 | 9/1989 |
| WO | 2009126933 A2 | 10/2009 |

OTHER PUBLICATIONS

Webb et al., Journal of the Chemical Society Journal (1962), pp. 4307-4319.*
Webb et al., Journal of the Chemical Society Journal (1962), pp. 4320-4323.*
International Search Report and Written Opinion for corresponding International Application No. PCT/CN2011/076980, dated Oct. 13, 2011.
International Search Report and Written Opinion for corresponding International Application No. PCT/US2013/044346, dated Nov. 5, 2013.

(Continued)

Primary Examiner — Brian J Davis
(74) Attorney, Agent, or Firm — Goodwin Procter LLP

(57) ABSTRACT

The present invention relates to the reduction of polycyano compounds to produce polyamines, in particular diaminoacetal and diaminoketal compounds, and their use as curing agents in epoxy resin compositions. The reduction with molecular hydrogen can be carried out using a metal catalyst selected from GROUP VIII and a catalytic promoter. The reduction can include anhydrous or aqueous ammonia. The reaction can be carried out in continuous and batch modes with catalyst and solvent recycling. The epoxy resin composition consisting of an epoxy resin and a polyamine curing agent that can be used in fiber-reinforced composite materials, coating materials, and the like.

54 Claims, 3 Drawing Sheets

(56) References Cited

OTHER PUBLICATIONS

International Search Report and Written Opinion for corresponding International Application No. PCT/US2014/060524, dated Mar. 19, 2015.
Paramonov et al., "Fully Acid-Degradable Biocompatible Polyacetal Microparticles for Drug Delivery", Bioconjugate Chem., vol. 19, No. 4, (2008), pp. 911-919.
Shim et al., "Acid-Responsive Linear Polyethylenimine for Efficient, Specific, and Biocompatible siRNA Delivery", Bioconjugate Chem., vol. 20, No. 3, (2009), pp. 488-499.
Bassampour et al., "Degradable epoxy resins based on bisphenol A diglycidyl ether and silyl ether amine curing agents", Journal of Applied Polymer Science, (2017), App 44620, pp. 1-9.
Bradley et al., "Alkoxides of vanadium (IV)", Canadian Journal of Chemistry (1962), vol. 40, pp. 1183-1188.
Bunyan et al., "Reactivity of organophosphorus compounds. XIII. Radical-chain transfer reactions of triethyl phosphite: a new phosphorothiolate synthesis", Journal of the Chemical Society (1962), pp. 2953-2958.
Emblem et al., "Preparation and properties of some aminoalkoxysilanes", Journal of Applied Chemistry (1962), vol. 12, pp. 5-9.

\* cited by examiner

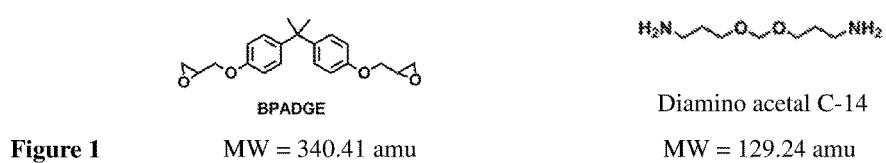
Figure 1  BPADGE  MW = 340.41 amu    Diamino acetal C-14  MW = 129.24 amu
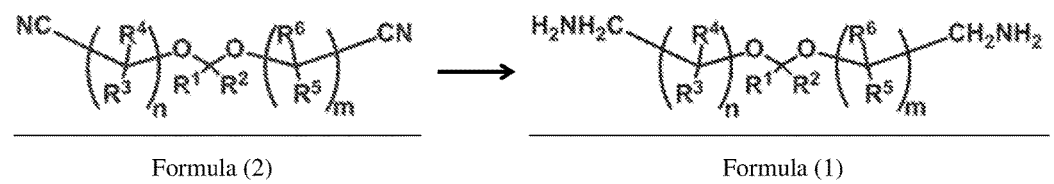
Formula (2) → Formula (1)
Figure 2

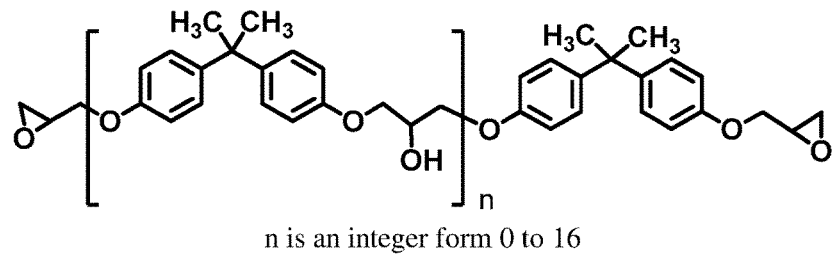
n is an integer form 0 to 16
DGEBPA or BPADGE
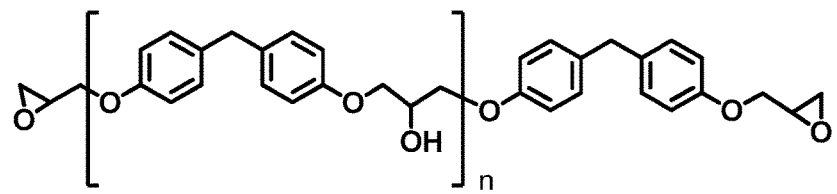
n is an integer form 0 to 16
DGEBPF or BPFDGE
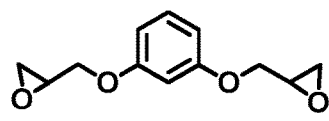
Diepoxide
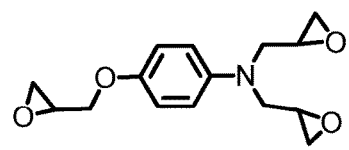
Triepoxide resin
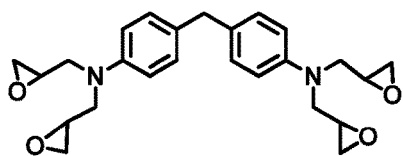
A tretra epoxide resin
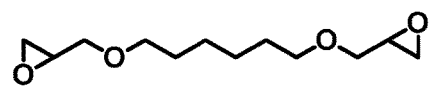
1,6-Hexanediol diglycidyl ether
Figure 4.

SYNTHESIS OF AND COMPOSITIONS CONTAINING DIAMINOACETALS AND DIAMINOKETALS

CROSS-REFERENCE TO RELATED PATENT APPLICATIONS

This application is a continuation of Ser. No. 14/406,095, filed Dec. 5, 2014, which is a national stage application under U.S.C. § 371 of International Application No. PCT/US2013/044346, filed Jun. 5, 2013, which claims priority to U.S. Patent Application No. 61/655,794, filed Jun. 5, 2012, the contents of each of which are incorporated herein in their entirety.

BACKGROUND

The present invention generally relates to chemical synthesis of polyamine compounds, in particular chemical synthesis diaminoacetal and diaminoketal compounds, and compositions containing these compounds and uses of the these compositions.

BRIEF SUMMARY OF THE INVENTION

In one aspect, the present invention provides a process for preparing a polyamine compound represented by Formula (1) from a polycyano compound represented by Formula (2):

Formula (1)

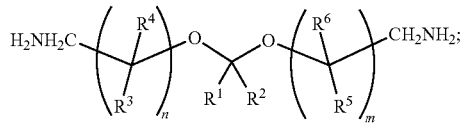

Formula (2)

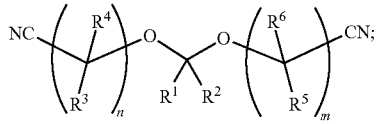

wherein: each of $R^1$ and $R^2$ is independently selected from the group consisting of hydrogen, alkyl group, cycloalkyl group and aromatic group; both of $R^1$ and $R^2$ can form a cyclic radical; each of $R^3$, $R^4$, $R^5$ and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 1 to 20. In one embodiment, the process comprises reducing the polycyano compound of Formula (2) with a reducing agent to produce the polyamine compound of Formula (1). In one embodiment, the reducing agent comprises molecular hydrogen. In one embodiment, the reduction is carried out in the presence of a catalyst. In one embodiment, the catalyst comprises one or more Group VIII metals. In one embodiment, the catalyst comprises one or more Group VIII metals selected from the group consisting of nickel, palladium, platinum, ruthenium, rhodium and cobalt.

In another aspect, the present invention provides an epoxy resin composition for fiber-reinforced composite materials, for coating materials, for encapsulating materials, and/or adhesives. In one embodiment, the epoxy resin composition comprises an epoxy resin; and an amine curing agent, the amine curing agent comprising a polyamine compound having Formula (1):

Formula (1)

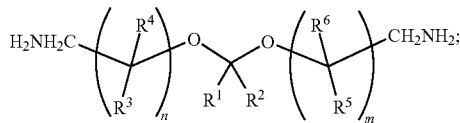

wherein: each of $R^1$ and $R^2$ is independently selected from the group consisting of hydrogen, alkyl group, cycloalkyl group and aromatic group; or both of $R^1$ and $R^2$ forms a cyclic radical; each of $R^3$, $R^4$, $R^5$ and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 1 to 20. In one embodiment, the epoxy resin comprises an average of at least two epoxide groups per molecule. In one embodiment, the epoxy resin has two epoxide groups per molecule (a diepoxide epoxy resin). In one embodiment, the diepoxide epoxy resin is selected from the group consisting of glycidyl ether epoxy resin, glycidyl ester epoxy resin, glycidyl amine epoxy resin, alicyclic epoxy resin, aliphatic epoxy resin, and phenolic epoxy resin.

In another aspect, the present invention provides a method of curing an epoxy resin formulation. In one embodiment, the method of curing an epoxy resin formulation cures the epoxy resin to a degree of cure of at least about 50% or more. In one embodiment, the curing of the epoxy resin formulation comprises heating the epoxy resin formulation. In one embodiment, the method of curing the epoxy resin formulation comprises (i) providing an epoxy resin composition in accordance with the present invention; and (ii) heating the epoxy resin composition. In one embodiment, the method of curing the epoxy resin formulation further includes adding a reinforcing agent to produce a reinforced cured epoxy resin composition.

In another aspect, the present invention provides a cross-linked polymer matrix in which the cross-linked polymer is derived from an epoxy resin having at least two epoxide groups and a cross-linking group derived from a curing agent represented by Formula (1):

Formula (1)

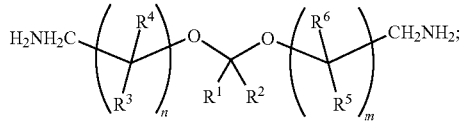

wherein: each of $R^1$ and $R^2$ is independently selected from the group consisting of hydrogen, alkyl group, cycloalkyl group and aromatic group; both of $R^1$ and $R^2$ can form a cyclic radical; each of $R^3$, $R^4$, $R^5$ and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 0 to 20. In one embodiment, the epoxy resin has two epoxide per molecule. In one embodiment, the epoxy resin is selected from the group consisting of glycidyl ether epoxy resin, glycidyl ester epoxy resin, glycidyl amine epoxy resin, alicyclic epoxy resin, aliphatic epoxy resin, phenolic epoxy resin, and combinations thereof.

In another aspect, the present invention provides a method for recycling a reinforced composite in accordance with the present invention. In one embodiment, the method for recycling the reinforced composite comprises a step of degrading the cross-linked polymer matrix using an acid. In one embodiment, the degradation of the cross-linked polymer matrix is carried out using an acid in the presence of a solvent. In one embodiment, the degradation of the cross-linked polymer matrix is carried out using an acid under a heating condition.

In another aspect, the present invention relates to a degradation product resulting from the method for recycling the reinforced composite according to the present invention.

In another aspect, the present invention relates to the use of any of the epoxy compositions of the present invention as an adhesive, a coating material, or an encapsulating material; wherein the epoxy composition can be removed, recycled, or dissolved from the article in contact with said epoxy composition via the method of degrading the epoxy composition according to the present invention.

BRIEF DESCRIPTION OF THE DRAWINGS

FIG. 1 shows structures of BPADGE and Diamino acetal C-14 of Example 14;

FIG. 2 shows a generic scheme for the conversion of polycyano compounds of Formula (2) into polyamino compounds of Formula (1);

FIG. 4 shows examples of epoxy resins that can be used in accordance with exemplary embodiments of the present invention.

DETAILED DESCRIPTION

Figure 3:
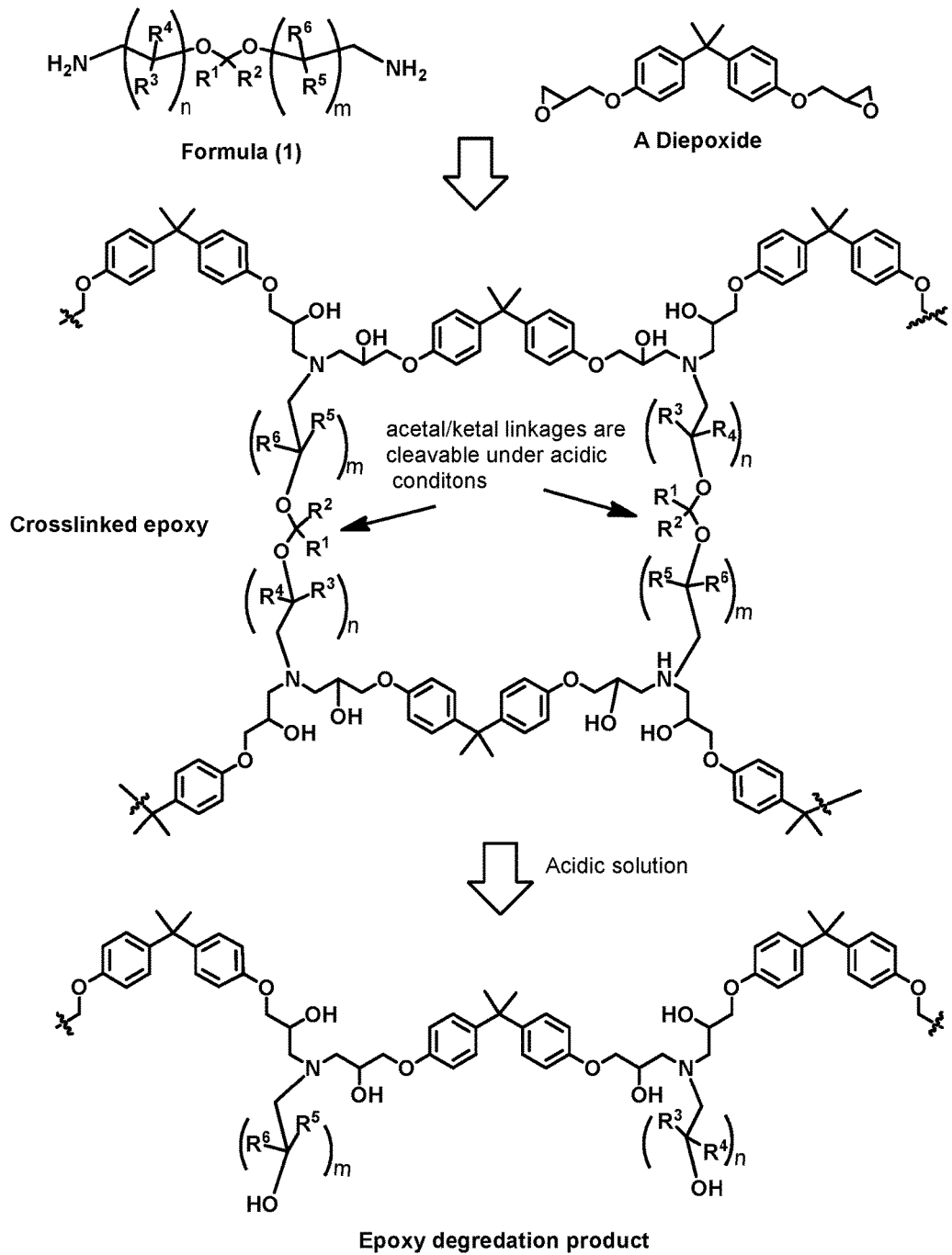
FIG. 3 shows generic cross-linked epoxy product and generic epoxy degradation product.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

In an aspect, the present invention relates to diaminoacetals, to processes for their preparation, and especially to their preparation from dicyanoacetals. The over-all process of this invention includes two steps. In the first step, dicyanoacetals are prepared by the reaction of a compound containing both an alcohol group and a cyano group (now, herein referred to as a cyanohydrin) with an aldehyde or ketone, (or an aldehyde or ketone equivalent). In the second step the dicyanoacetal is hydrogenated to give the corresponding diaminoacetal. The primary embodiment of the present invention is the preparation of diaminoacetal compounds from dicyanoacetal compounds.

I. PROCESS FOR MAKING POLYAMINES

The present invention provides an efficient process for the preparation of the polyamine compound represented by Formula (1):

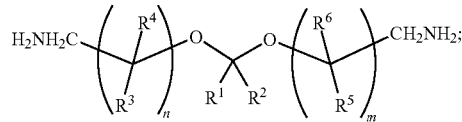

Formula (1)

from a polycyano compound of Formula (2):

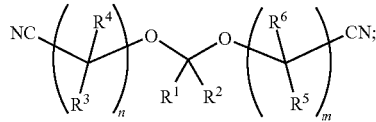

Formula (2)

wherein: each of $R^1$ and $R^2$ is independently selected from the group consisting of hydrogen, alkyl group, cycloalkyl group and aromatic group; or both of $R^1$ and $R^2$ forms a cyclic radical; each of $R^3$, $R^4$, $R^5$ and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 1 to 20; the process comprising reducing the compound of Formula (2) with a reducing agent to produce the compound of Formula (1).

Formula (1) represents a class of polyamine molecules that depending on the exact nature of $R^1$ and $R^2$ can be subdivided into three classes: (i) polyaminoformal ($R^1$=H; and $R^2$=H); (ii) polyaminoacetal (e.g., $R^1$=H; and $R^2$=carbon fragment); and (ii) polyaminoketal (e.g., $R^1$=carbon fragment; and $R^2$=carbon fragment). Individually, the molecules classified according to Formula (1) may contain an acetal group, ketal group, or a formal group, that connects the polyamine groups.

Referring to the compounds of Formulas (1) and (2), in one embodiment, each of $R^1$ and $R^2$ is independently an alkyl group. In one embodiment, each of $R^1$ and $R^2$ is independently a $C_1$-$C_{20}$ alkyl group. In one embodiment, each of $R^1$ and $R^2$ is independently a $C_1$-$C_{15}$ alkyl group. In one embodiment, each of $R^1$ and $R^2$ is independently a $C_1$-$C_{10}$ alkyl group. In one embodiment, each of $R^1$ and $R^2$ is independently a $C_1$-$C_5$ alkyl group. In one embodiment, each of $R^1$ and $R^2$ is independently a $C_1$-$C_3$ alkyl group. In one embodiment, each of $R^1$ and $R^2$ is independently a $C_1$-$C_2$ alkyl group. In one embodiment, each of $R^1$ and $R^2$ is independently a $C_1$ alkyl group. In one embodiment, each of $R^1$ and $R^2$ is independently selected from the group consisting of $C_1$ (e.g., methyl); $C_2$ (e.g., ethyl); $C_3$ (e.g., propyl); $C_4$ (e.g., n-butyl & isobutyl); $C_5$ (e.g., pentyl, isopentyl, neopentyl); and $C_6$ (e.g., hexyl, 2-Methylpentyl; 3-Methylpentyl; 2,3-Dimethylbutyl; 2,2-Dimethylbutyl). In one embodiment, each of $R^1$ and $R^2$ is independent selected from the group consisting of methyl, ethyl, propyl, isopropyl, butyl, isobutyl, tert-butyl, amyl, isoamyl, pentyl, sec-butyl, isopentyl, neopentyl, heptyl, hexyl, octyl, decyl, dodecyl, and hexadecyl. In one embodiment, each of $R^1$ and $R^2$ is independent selected from the group consisting of methyl, ethyl, propyl, butyl, pentyl, hexyl, heptyl, octyl, nonyl, decyl, undecyl, dodecyl, hexadecyl, and icosyl.

In one embodiment, each of $R^1$ and $R^2$ is independently a cycloalkyl group. In one embodiment, each of $R^1$ and $R^2$ is independently a cycloalkyl group. In one embodiment, each of $R^1$ and $R^2$ is independently a $C_3$-$C_{20}$ cycloalkyl group. In one embodiment, each of $R^1$ and $R^2$ is independently a $C_3$-$C_{15}$ cycloalkyl group. In one embodiment, each of $R^1$ and $R^2$ is independently a $C_3$-$C_{10}$ cycloalkyl group. In one embodiment, each of $R^1$ and $R^2$ is independently a $C_3$-$C_5$ cycloalkyl group. In one embodiment, each of $R^1$ and $R^2$ is independently selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

In one embodiment, each of $R^1$ and $R^2$ is independently an aryl group. The term "aryl" as used herein refers to any functional group or substituent derived from an aromatic ring, be it phenyl, naphthyl, thienyl, indolyl, or the like. Examples of aryl include, but are not limited to, phenyl, tolyl, xylyl, naphthyl, biphenylyl, benzyl, and phenylethyl groups.

In one embodiment, both $R^1$ and $R^2$ can form a cyclic group. The cyclic group is not particularly limited. It can be a carbocycle, a cycloalkyl, an aryl, a heterocycle, a heteroaryl, an aralkyl or any suitable cyclic group. In one embodiment, the cyclic group is selected from the group consisting of cycloalkyl, cycloalkyl aryl, heterocyclic, alkylaryl, alkylheterocycle and arylheterocycle groups.

In one embodiment, each of $R^3$, $R^4$, $R^5$ and $R^6$ is independently an alkyl group.

In one embodiment, each of $R^3$, $R^4$, $R^5$ and $R^6$ is independently a $C_1$-$C_{20}$ alkyl group. In one embodiment, each of $R^3$, $R^4$, $R^5$ and $R^6$ is independently a $C_1$-$C_{15}$ alkyl group. In one embodiment, each of $R^3$, $R^4$, $R^5$ and $R^6$ is independently a $C_1$-$C_{10}$ alkyl group. In one embodiment, each of $R^3$, $R^4$, $R^5$ and $R^6$ is independently a $C_1$-$C_5$ alkyl group. In one embodiment, each of $R^3$, $R^4$, $R^5$ and $R^6$ is independently a $C_1$-$C_3$ alkyl group. In one embodiment, each of $R^3$, $R^4$, $R^5$ and $R^6$ is independently a $C_1$-$C_2$ alkyl group. In one embodiment, each of $R^3$, $R^4$, $R^5$ and $R^6$ is independently a $C_1$ alkyl group. In one embodiment, each of $R^3$, $R^4$, $R^5$ and $R^6$ is independently selected from the group consisting of $C_1$ (e.g., methyl); $C_2$ (e.g., ethyl); $C_3$ (e.g., propyl); $C_4$ (e.g., n-butyl & isobutyl); $C_5$ (e.g., pentyl, isopentyl, neopentyl); and $C_6$ (e.g., hexyl, 2-Methylpentyl; 3-Methylpentyl; 2,3-Dimethylbutyl; 2,2-Dimethylbutyl). In one embodiment, each of $R^3$, $R^4$, $R^5$ and $R^6$ is independent selected from the group consisting of methyl, ethyl, propyl, isopropyl, butyl, isobutyl, tert-butyl, amyl, isoamyl, pentyl, sec-butyl, isopentyl, neopentyl, heptyl, hexyl, octyl, decyl, dodecyl, and hexadecyl. In one embodiment, each of $R^3$, $R^4$, $R^5$ and $R^6$ is independent selected from the group consisting of methyl, ethyl, propyl, butyl, pentyl, hexyl, heptyl, octyl, nonyl, decyl, undecyl, dodecyl, hexadecyl, and icosyl.

In one embodiment, each of $R^3$, $R^4$, $R^5$ and $R^6$ is independently a cycloalkyl group. In one embodiment, each of $R^3$, $R^4$, $R^5$ and $R^6$ is independently a cycloalkyl group. In one embodiment, each of $R^3$, $R^4$, $R^5$ and $R^6$ is independently a $C_3$-$C_{20}$ cycloalkyl group. In one embodiment, each of $R^3$, $R^4$, $R^5$ and $R^6$ is independently a $C_3$-$C_{10}$ cycloalkyl group. In one embodiment, each of $R^3$, $R^4$, $R^5$ and $R^6$ is independently a $C_1$-$C_5$ cycloalkyl group. In one embodiment, each of $R^3$, $R^4$, $R^5$ and $R^6$ is independently selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

In one embodiment, each of $R^3$, $R^4$, $R^5$ and $R^6$ is independently an aryl group. As stated elsewhere herein, the term "aryl" refers to any functional group or substituent derived from an aromatic ring, be it phenyl, naphthyl, thienyl, indolyl, or the like. Examples of suitable aryl groups include, but are not limited to, phenyl, tolyl, xylyl, naphthyl, biphenylyl, benzyl, and phenylethyl groups.

In one embodiment, both $R^3$ and $R^4$ can combine with each other to form a cyclic radical. In one embodiment, both $R^3$ and $R^4$ combine with each other to form a $C_3$-$C_{20}$ cycloalkyl group. In one embodiment, both $R^3$ and $R^4$ combine with each other to form a $C_3$-$C_{15}$ cycloalkyl group. In one embodiment, both $R^3$ and $R^4$ combine with each other to form a $C_3$-$C_{10}$ cycloalkyl group. In one embodiment, both $R^3$ and $R^4$ combine with each other to form a $C_3$-$C_5$ cycloalkyl group. In one embodiment, both $R^3$ and $R^4$ combine with each other to form a cyclic group selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

In one embodiment, $R^5$ and $R^6$ can combine with each other to form a cyclic radical. In one embodiment, both $R^5$ and $R^6$ can combine with each other to form a cyclic radical. In one embodiment, both $R^5$ and $R^6$ combine with each other to form a $C_3$-$C_{20}$ cycloalkyl group. In one embodiment, both $R^5$ and $R^6$ combine with each other to form a $C_3$-$C_{15}$ cycloalkyl group. In one embodiment, both $R^5$ and $R^6$ combine with each other to form a $C_3$-$C_{10}$ cycloalkyl group. In one embodiment, both $R^5$ and $R^6$ combine with each other to form a $C_3$-$C_5$ cycloalkyl group. In one embodiment, both $R^5$ and $R^6$ combine with each other to form a cyclic group selected from the group consisting of cyclopropylalkyl (e.g., cyclopropylmethyl), cyclobutylalkyl (e.g., cyclobutylmethyl), cyclopentylalkyl (e.g. cyclopentylmethyl), cyclohexylalkyl (e.g. cyclohexylmethyl), cyclopropyl, cyclobutyl, cyclopentyl, and cyclohexyl.

Each m and n in the polyamine and polycyano compounds represented by Formulas (1) and (2) is independently an integer ranging from 1 to 20. In one embodiment, each m and n is independently an integer selected from the group consisting of 1, 2, 3, 4, 5, 6, 7, 8, 9, 10, 11, 12, 13, 14, 15, 16, 17, 18, 19, and 20.

The process of making the polyamine of Formula (1) from the polycyano Formula (2) employs a reducing agent. Any suitable reducing agent can be used in this process. In one embodiment, the reducing agent comprises molecular hydrogen. In one embodiment, the reduction is carried out at molecular hydrogen pressure of from about 80 psi to about 3000 psi. In one embodiment, the reduction is carried out at molecular hydrogen pressure selected from the group consisting of about 80 psi, about 160 psi, about 240 psi, about 320 psi, about 400 psi, about 480 psi, about 560 psi, about 640 psi, about 720 psi, about 800 psi, about 880 psi, about 960 psi, about 1040 psi, about 1120 psi, about 1200 psi, about 1280 psi, about 1360 psi, about 1440 psi, about 1520 psi, about 1600 psi, about 1680 psi, about 1760 psi, about 1840 psi, about 1920 psi, about 2000 psi, about 2080 psi, about 2160 psi, about 2240 psi, about 2320 psi, about 2400 psi, about 2480 psi, about 2560 psi, about 2640 psi, about 2720 psi, about 2800 psi, about 2880 psi, about 2960 psi, and about 3040 psi. In one embodiment, the reduction is carried out at molecular hydrogen pressure selected from the group consisting of less than about 80 psi, less than about 160 psi, less than about 240 psi, less than about 320 psi, less than about 400 psi, less than about 480 psi, less than about 560 psi, less than about 640 psi, less than about 720 psi, less than about 800 psi, less than about 880 psi, less than about 960 psi, less than about 1040 psi, less than about 1120 psi, less than about 1200 psi, less than about 1280 psi, less than about 1360 psi, less than about 1440 psi, less than about 1520 psi, less than about 1600 psi, less than about 1680 psi, less than about 1760 psi, less than about 1840 psi, less than about 1920 psi, less than about 2000 psi, less than about 2080 psi, less than about 2160 psi, less than about 2240 psi, less than about 2320 psi, less than about 2400 psi, less than about 2480 psi, less than about 2560 psi, less than about 2640 psi, less than about 2720 psi, less than about 2800 psi, less than about 2880 psi, less than about 2960 psi, and less than about 3040 psi. In one embodiment, the reduction is carried out at molecular hydrogen pressure of from about 100 psi to about 1500 psi.

In some embodiments, the reduction is carried out at molecular hydrogen pressure of at least 80 psi. In some embodiments, the reduction is carried out at molecular hydrogen pressure selected from the group consisting of about less than about 1500 psi but equal to or greater than about 80 psi, less than about 1450 psi but equal to or greater than about 80 psi, less than about 1400 psi but equal to or greater than about 80 psi, less than about 1350 psi but equal to or greater than about 80 psi, less than about 1300 psi but equal to or greater than about 80 psi, less than about 1250 psi but equal to or greater than about 80 psi, less than about 1200 psi but equal to or greater than about 80 psi, less than about 1150 psi but equal to or greater than about 80 psi, less than about 1100 psi but equal to or greater than about 80 psi, less than about 1050 psi but equal to or greater than about 80 psi, less than about 1000 psi but equal to or greater than about 80 psi, less than about 950 psi but equal to or greater than about 80 psi, less than about 900 psi but equal to or greater than about 80 psi, less than about 850 psi but equal to or greater than about 80 psi, less than about 800 psi but equal to or greater than about 80 psi, less than about 750 psi but equal to or greater than about 80 psi, less than about 700 psi but equal to or greater than about 80 psi, less than about 650 psi but equal to or greater than about 80 psi, less than about 600 psi but equal to or greater than about 80 psi, less than about 550 psi but equal to or greater than about 80 psi, less than about 500 psi but equal to or greater than about 80 psi, less than about 450 psi but equal to or greater than about 80 psi, less than about 400 psi but equal to or greater than about 80 psi, less than about 350 psi but equal to or greater than about 80 psi, less than about 300 psi but equal to or greater than about 80 psi, less than about 250 psi but equal to or greater than about 80 psi, less than about 200 psi but equal to or greater than about 80 psi, less than about 150 psi but equal to or greater than about 80 psi, and less than about 100 psi but equal to or greater than about 80 psi.

In some embodiments, the process of making the polyamine of Formula (1) from the polycyano Formula (2) employs a reducing agent and a catalyst. In one embodiment, the reduction is carried out in the presence of a metal-containing catalyst. In one embodiment, the metal-containing catalyst comprises one or more Group VIII metal. In one embodiment, the catalyst contains a metal or pseudo-metal selected from a group consisting of Raney nickel, Sponge nickel, palladium, platinum, cobalt, copper, copper oxide, Lindlar catalyst, rhodium, platinum dioxide, sodium borohydride, lithium aluminum hydride, nickel, ruthenium, iron, tellurium, copper triphenylphosphine complexes, ruthenium phosphine complexes, rhodium carbonyl clusters, palladium on carbon, and complexes of palladium with quinoline, pyridine, and phenylisocyano ligands. In one embodiment, the catalyst contains a metal selected from the group consisting of nickel, palladium, platinum, ruthenium, rhodium and cobalt.

When a catalyst is employed in the process of making the polyamine of Formula (1), any suitable amount of the catalyst can be used. In one embodiment, the reduction step is carried out in the presence of a catalyst present in an amount ranging from about 0.1 wt. % to about 120 wt. % of the polycyano compound of Formula (2). In one embodiment, the reduction step is carried out in the presence of a catalyst present in an amount selected from the group consisting of about 120 wt. % but equal to or greater than about 0.1 wt. %, less than about 115 wt. % but equal to or greater than about 0.1 wt. %, less than about 110 wt. % but equal to or greater than about 0.1 wt. %, less than about 105 wt. % but equal to or greater than about 0.1 wt. %, less than about 100 wt. % but equal to or greater than about 0.1 wt. %, less than about 95 wt. % but equal to or greater than about 0.1 wt. %, less than about 90 wt. % but equal to or greater than about 0.1 wt. %, less than about 85 wt. % but equal to or greater than about 0.1 wt. %, less than about 80 wt. % but equal to or greater than about 0.1 wt. %, less than about 75 wt. % but equal to or greater than about 0.1 wt. %, less than about 70 wt. % but equal to or greater than about 0.1 wt. %, less than about 65 wt. % but equal to or greater than about 0.1 wt. %, less than about 60 wt. % but equal to or greater than about 0.1 wt. %, less than about 55 wt. % but equal to or greater than about 0.1 wt. %, less than about 50 wt. % but equal to or greater than about 0.1 wt. %, less than about 45 wt. % but equal to or greater than about 0.1 wt. %, less than about 40 wt. % but equal to or greater than about 0.1 wt. %, less than about 35 wt. % but equal to or greater than about 0.1 wt. %, less than about 30 wt. % but equal to or greater than about 0.1 wt. %, less than about 25 wt. % but equal to or greater than about 0.1 wt. %, less than about 20 wt. % but equal to or greater than about 0.1 wt. %, less than about 15 wt. % but equal to or greater than about 0.1 wt. %, less than about 10 wt. % but equal to or greater than about 0.1 wt. %, and less than about 5 wt. % but equal to or greater than about 0.1 wt. %, wherein the percentages are wt. % of the polycyano compound of Formula (2).

In one embodiment, the reduction step is carried out in the presence of a catalyst present in an amount selected from the group consisting of about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2 wt. %, about 2.1 wt. %, about 2.2 wt. %, about 2.3 wt. %, about 2.4 wt. %, about 2.5 wt. %, about 2.6 wt. %, about 2.7 wt. %, about 2.8 wt. %, about 2.9 wt. %, about 3 wt. %, about 3.1 wt. %, about 3.2 wt. %, about 3.3 wt. %, about 3.4 wt. %, about 3.5 wt. %, about 3.6 wt. %, about 3.7 wt. %, about 3.8 wt. %, about 3.9 wt. %, about 4 wt. %, about 4.1 wt. %, about 4.2 wt. %, about 4.3 wt. %, about 4.4 wt. %, about 4.5 wt. %, about 4.6 wt. %, about 4.7 wt. %, about 4.8 wt. %, about 4.9 wt. %, about 5 wt. %, about 5.1 wt. %, about 5.2 wt. %, about 5.3 wt. %, about 5.4 wt. %, about 5.5 wt. %, about 5.6 wt. %, about 5.7 wt. %, about 5.8 wt. %, about 5.9 wt. %, about 6 wt. %, about 6.1 wt. %, about 6.2 wt. %, about 6.3 wt. %, about 6.4 wt. %, about 6.5 wt. %, about 6.6 wt. %, about 6.7 wt. %, about 6.8 wt. %, about 6.9 wt. %, about 7 wt. %, about 7.1 wt. %, about 7.2 wt. %, about 7.3 wt. %, about 7.4 wt. %, about 7.5 wt. %, about 7.6 wt. %, about 7.7 wt. %, about 7.8 wt. %, about 7.9 wt. %, about 8 wt. %, about 8.1 wt. %, about 8.2 wt. %, about 8.3 wt. %, about 8.4 wt. %, about 8.5 wt. %, about 8.6 wt. %, about 8.7 wt. %, about 8.8 wt. %, about 8.9 wt. %, about 9 wt. %, about 9.1 wt. %, about 9.2 wt. %, about 9.3 wt. %, about 9.4 wt. %, about 9.5 wt. %, about 9.6 wt. %, about 9.7 wt. %, about 9.8 wt. %, about 9.9 wt. %, about 10 wt. %, about 10.1 wt. %, about 10.2 wt. %, about 10.3 wt. %, about 10.4 wt. %, about 10.5 wt. %, about 10.6 wt. %, about 10.7 wt. %, about 10.8 wt. %, about 10.9 wt. %, about 11 wt. %, about 11.1 wt. %, about 11.2 wt. %, about 11.3 wt. %, about 11.4 wt. %, about 11.5 wt. %, about 11.6 wt. %, about 11.7 wt. %, about 11.8 wt. %, about 11.9 wt. %, about 12 wt. %, about 12.1 wt. %, about 12.2 wt. %, about 12.3 wt. %, about 12.4 wt. %, about 12.5 wt. %, about 12.6 wt. %, about 12.7 wt. %, about 12.8 wt. %, about 12.9 wt. %, about 13 wt. %, about 13.1 wt. %, about 13.2 wt. %, about 13.3 wt. %, about 13.4 wt. %, about 13.5 wt. %, about 13.6 wt. %, about 13.7 wt. %, about 13.8 wt. %, about 13.9 wt. %, about 14 wt. %, about 14.1 wt. %, about 14.2 wt. %, about 14.3 wt. %, about 14.4 wt. %, about 14.5 wt. %, about 14.6 wt. %, about 14.7 wt. %, about 14.8 wt. %, about 14.9 wt. %, about 15 wt. %, about 15.1 wt. %, about 15.2 wt. %, about 15.3 wt. %, about 15.4 wt. %, about 15.5 wt. %, about 15.6 wt. %, about 15.7 wt. %, about 15.8 wt. %, about 15.9 wt. %, about 16 wt. %, about 16.1 wt. %, about 16.2 wt. %, about 16.3 wt. %, about 16.4 wt. %, about 16.5 wt. %, about 16.6 wt. %, about 16.7 wt. %, about 16.8 wt. %, about 16.9 wt. %, about 17 wt. %, about 17.1 wt. %, about 17.2 wt. %, about 17.3 wt. %, about 17.4 wt. %, about 17.5 wt. %, about 17.6 wt. %, about 17.7 wt. %, about 17.8 wt. %, about 17.9 wt. %, about 18 wt. %, about 18.1 wt. %, about 18.2 wt. %, about 18.3 wt. %, about 18.4 wt. %, about 18.5 wt. %, about 18.6 wt. %, about 18.7 wt. %, about 18.8 wt. %, about 18.9 wt. %, about 19 wt. %, about 19.1 wt. %, about 19.2 wt. %, about 19.3 wt. %, about 19.4 wt. %, about 19.5 wt. %, about 19.6 wt. %, about 19.7 wt. %, about 19.8 wt. %, about 19.9 wt. %, about 20 wt. %, about 20.1 wt. %, about 20.2 wt. %, about 20.3 wt. %, about 20.4 wt. %, about 20.5 wt. %, about 20.6 wt. %, about 20.7 wt. %, about 20.8 wt. %, about 20.9 wt. %, about 21 wt. %, about 21.1 wt. %, about 21.2 wt. %, about 21.3 wt. %, about 21.4 wt. %, about 21.5 wt. %, about 21.6 wt. %, about 21.7 wt. %, about 21.8 wt. %, about 21.9 wt. %, about 22 wt. %, about 22.1 wt. %, about 22.2 wt. %, about 22.3 wt. %, about 22.4 wt. %, about 22.5 wt. %, about 22.6 wt. %, about 22.7 wt. %, about 22.8 wt. %, about 22.9 wt. %, about 23 wt. %, about 23.1 wt. %, about 23.2 wt. %, about 23.3 wt. %, about 23.4 wt. %, about 23.5 wt. %, about 23.6 wt. %, about 23.7 wt. %, about 23.8 wt. %, about 23.9 wt. %, about 24 wt. %, about 24.1 wt. %, about 24.2 wt. %, about 24.3 wt. %, about 24.4 wt. %, about 24.5 wt. %, about 24.6 wt. %, about 24.7 wt. %, about 24.8 wt. %, about 24.9 wt. %, about 25 wt. %, about 25.1 wt. %, about 25.2 wt. %, about 25.3 wt. %, about 25.4 wt. %, about 25.5 wt. %, about 25.6 wt. %, about 25.7 wt. %, about 25.8 wt. %, about 25.9 wt. %, about 26 wt. %, about 26.1 wt. %, about 26.2 wt. %, about 26.3 wt. %, about 26.4 wt. %, about 26.5 wt. %, about 26.6 wt. %, about 26.7 wt. %, about 26.8 wt. %, about 26.9 wt. %, about 27 wt. %, about 27.1 wt. %, about 27.2 wt. %, about 27.3 wt. %, about 27.4 wt. %, about 27.5 wt. %, about 27.6 wt. %, about 27.7 wt. %, about 27.8 wt. %, about 27.9 wt. %, about 28 wt. %, about 28.1 wt. %, about 28.2 wt. %, about 28.3 wt. %, about 28.4 wt. %, about 28.5 wt. %, about 28.6 wt. %, about 28.7 wt. %, about 28.8 wt. %, about 28.9 wt. %, about 29 wt. %, about 29.1 wt. %, about 29.2 wt. %, about 29.3 wt. %, about 29.4 wt. %, about 29.5 wt. %, about 29.6 wt. %, about 29.7 wt. %, about 29.8 wt. %, about 29.9 wt. %, about 30 wt. %, about 30.1 wt. %, about 30.2 wt. %, about 30.3 wt. %, about 30.4 wt. %, about 30.5 wt. %, about 30.6 wt. %, about 30.7 wt. %, about 30.8 wt. %, about 30.9 wt. %, about 31 wt. %, about 31.1 wt. %, about 31.2 wt. %, about 31.3 wt. %, about 31.4 wt. %, about 31.5 wt. %, about 31.6 wt. %, about 31.7 wt. %, about 31.8 wt. %, about 31.9 wt. %, about 32 wt. %, about 32.1 wt. %, about 32.2 wt. %, about 32.3 wt. %, about 32.4 wt. %, about 32.5 wt. %, about 32.6 wt. %, about 32.7 wt. %, about 32.8 wt. %, about 32.9 wt. %, about 33 wt. %, about 33.1 wt. %, about 33.2 wt. %, about 33.3 wt. %, about 33.4 wt. %, about 33.5 wt. %, about 33.6 wt. %, about 33.7 wt. %, about 33.8 wt. %, about 33.9 wt. %, about 34 wt. %, about 34.1 wt. %, about 34.2 wt. %, about 34.3 wt. %, about 34.4 wt. %, about 34.5 wt. %, about 34.6 wt. %, about 34.7 wt. %, about 34.8 wt. %, about 34.9 wt. %, about 35 wt. %, about 35.1 wt. %, about 35.2 wt. %, about 35.3 wt. %, about 35.4 wt. %, about 35.5 wt. %, about 35.6 wt. %, about 35.7 wt. %, about 35.8 wt. %, about 35.9 wt. %, about 36 wt. %, about 36.1 wt. %, about 36.2 wt. %, about 36.3 wt. %, about 36.4 wt. %, about 36.5 wt. %, about 36.6 wt. %, about 36.7 wt. %, about 36.8 wt. %, about 36.9 wt. %, about 37 wt. %, about 37.1 wt. %, about 37.2 wt. %, about 37.3 wt. %, about 37.4 wt. %, about 37.5 wt. %, about 37.6 wt. %, about 37.7 wt. %, about 37.8 wt. %, about 37.9 wt. %, about 38 wt. %, about 38.1 wt. %, about 38.2 wt. %, about 38.3 wt. %, about 38.4 wt. %, about 38.5 wt. %, about 38.6 wt. %, about 38.7 wt. %, about 38.8 wt. %, about 38.9 wt. %, about 39 wt. %, about 39.1 wt. %, about 39.2 wt. %, about 39.3 wt. %, about 39.4 wt. %, about 39.5 wt. %, about 39.6 wt. %, about 39.7 wt. %, about 39.8 wt. %, about 39.9 wt. %, about 40 wt. %, about 40.1 wt. %, about 40.2 wt. %, about 40.3 wt. %, about 40.4 wt. %, about 40.5 wt. %, about 40.6 wt. %, about 40.7 wt. %, about 40.8 wt. %, about 40.9 wt. %, about 41 wt. %, about 41.1 wt. %, about 41.2 wt. %, about 41.3 wt. %, about 41.4 wt. %, about 41.5 wt. %, about 41.6 wt. %, about 41.7 wt. %, about 41.8 wt. %, about 41.9 wt. %, about 42 wt. %, about 42.1 wt. %, about 42.2 wt. %, about 42.3 wt. %, about 42.4 wt. %, about 42.5 wt. %, about 42.6 wt. %, about 42.7 wt. %, about 42.8 wt. %, about 42.9 wt. %, about 43 wt. %, about 43.1 wt. %, about 43.2 wt. %, about 43.3 wt. %, about 43.4 wt. %, about 43.5 wt. %, about 43.6 wt. %, about 43.7 wt. %, about 43.8 wt. %, about 43.9 wt. %, about 44 wt. %, about 44.1 wt. %, about 44.2 wt. %, about 44.3 wt. %, about 44.4 wt. %, about 44.5 wt. %, about 44.6 wt. %, about 44.7 wt. %, about 44.8 wt. %, about 44.9 wt. %, about 45 wt. %, about 45.1 wt. %, about 45.2 wt. %, about 45.3 wt. %, about 45.4 wt. %, about 45.5 wt. %, about 45.6 wt. %, about 45.7 wt. %, about 45.8 wt. %, about 45.9 wt. %, about 46 wt. %, about 46.1 wt. %, about 46.2 wt. %, about 46.3 wt. %, about 46.4 wt. %, about 46.5 wt. %, about 46.6 wt. %, about 46.7 wt. %, about 46.8 wt. %, about 46.9 wt. %, about 47 wt. %, about 47.1 wt. %, about 47.2 wt. %, about 47.3 wt. %, about 47.4 wt. %, about 47.5 wt. %, about 47.6 wt. %, about 47.7 wt. %, about 47.8 wt. %, about 47.9 wt. %, about 48 wt. %, about 48.1 wt. %, about 48.2 wt. %, about 48.3 wt. %, about 48.4 wt. %, about 48.5 wt. %, about 48.6 wt. %, about 48.7 wt. %, about 48.8 wt. %, about 48.9 wt. %, about 49 wt. %, about 49.1 wt. %, about 49.2 wt. %, about 49.3 wt. %, about 49.4 wt. %, about 49.5 wt. %, about 49.6 wt. %, about 49.7 wt. %, about 49.8 wt. %, about 49.9 wt. %, about 50 wt. %, about 50.1 wt. %, about 50.2 wt. %, about 50.3 wt. %, about 50.4 wt. %, about 50.5 wt. %, about 50.6 wt. %, about 50.7 wt. %, about 50.8 wt. %, about 50.9 wt. %, about 51 wt. %, about 51.1 wt. %, about 51.2 wt. %, about 51.3 wt. %, about 51.4 wt. %, about 51.5 wt. %, about 51.6 wt. %, about 51.7 wt. %, about 51.8 wt. %, about 51.9 wt. %, about 52 wt. %, about 52.1 wt. %, about 52.2 wt. %, about 52.3 wt. %, about 52.4 wt. %, about 52.5 wt. %, about 52.6 wt. %, about 52.7 wt. %, about 52.8 wt. %, about 52.9 wt. %, about 53 wt. %, about 53.1 wt. %, about 53.2 wt. %, about 53.3 wt. %, about 53.4 wt. %, about 53.5 wt. %, about 53.6 wt. %, about 53.7 wt. %, about 53.8 wt. %, about 53.9 wt. %, about 54 wt. %, about 54.1 wt. %, about 54.2 wt. %, about 54.3 wt. %, about 54.4 wt. %, about 54.5 wt. %, about 54.6 wt. %, about 54.7 wt. %, about 54.8 wt. %, about 54.9 wt. %, about 55 wt. %, about 55.1 wt. %, about 55.2 wt. %, about 55.3 wt. %, about 55.4 wt. %, about 55.5 wt. %, about 55.6 wt. %, about 55.7 wt. %, about 55.8 wt. %, about 55.9 wt. %, about 56 wt. %, about 56.1 wt. %, about 56.2 wt. %, about 56.3 wt. %, about 56.4 wt. %, about 56.5 wt. %, about 56.6 wt. %, about 56.7 wt. %, about 56.8 wt. %, about 56.9 wt. %, about 57 wt. %, about 57.1 wt. %, about 57.2 wt. %, about 57.3 wt. %, about 57.4 wt. %, about 57.5 wt. %, about 57.6 wt. %, about 57.7 wt. %, about 57.8 wt. %, about 57.9 wt. %, about 58 wt. %, about 58.1 wt. %, about 58.2 wt. %, about 58.3 wt. %, about 58.4 wt. %, about 58.5 wt. %, about 58.6 wt. %, about 58.7 wt. %, about 58.8 wt. %, about 58.9 wt. %, about 59 wt. %, about 59.1 wt. %, about 59.2 wt. %, about 59.3 wt. %, about 59.4 wt. %, about 59.5 wt. %, about 59.6 wt. %, about 59.7 wt. %, about 59.8 wt. %, about 59.9 wt. %, about 60 wt. %, about 60.1 wt. %, about 60.2 wt. %, about 60.3 wt. %, about 60.4 wt. %, about 60.5 wt. %, about 60.6 wt. %, about 60.7 wt. %, about 60.8 wt. %, about 60.9 wt. %, about 61 wt. %, about 61.1 wt. %, about 61.2 wt. %, about 61.3 wt. %, about 61.4 wt. %, about 61.5 wt. %, about 61.6 wt. %, about 61.7 wt. %, about 61.8 wt. %, about 61.9 wt. %, about 62 wt. %, about 62.1 wt. %, about 62.2 wt. %, about 62.3 wt. %, about 62.4 wt. %, about 62.5 wt. %, about 62.6 wt. %, about 62.7 wt. %, about 62.8 wt. %, about 62.9 wt. %, about 63 wt. %, about 63.1 wt. %, about 63.2 wt. %, about 63.3 wt. %, about 63.4 wt. %, about 63.5 wt. %, about 63.6 wt. %, about 63.7 wt. %, about 63.8 wt. %, about 63.9 wt. %, about 64 wt. %, about 64.1 wt. %, about 64.2 wt. %, about 64.3 wt. %, about 64.4 wt. %, about 64.5 wt. %, about 64.6 wt. %, about 64.7 wt. %, about 64.8 wt. %, about 64.9 wt. %, about 65 wt. %, about 65.1 wt. %, about 65.2 wt. %, about 65.3 wt. %, about 65.4 wt. %, about 65.5 wt. %, about 65.6 wt. %, about 65.7 wt. %, about 65.8 wt. %, about 65.9 wt. %, about 66 wt. %, about 66.1 wt. %, about 66.2 wt. %, about 66.3 wt. %, about 66.4 wt. %, about 66.5 wt. %, about 66.6 wt. %, about 66.7 wt. %, about 66.8 wt. %, about 66.9 wt. %, about 67 wt. %, about 67.1 wt. %, about 67.2 wt. %, about 67.3 wt. %, about 67.4 wt. %, about 67.5 wt. %, about 67.6 wt. %, about 67.7 wt. %, about 67.8 wt. %, about 67.9 wt. %, about 68 wt. %, about 68.1 wt. %, about 68.2 wt. %, about 68.3 wt. %, about 68.4 wt. %, about 68.5 wt. %, about 68.6 wt. %, about 68.7 wt. %, about 68.8 wt. %, about 68.9 wt. %, about 69 wt. %, about 69.1 wt. %, about 69.2 wt. %, about 69.3 wt. %, about 69.4 wt. %, about 69.5 wt. %, about 69.6 wt. %, about 69.7 wt. %, about 69.8 wt. %, about 69.9 wt. %, about 70 wt. %, about 70.1 wt. %, about 70.2 wt. %, about 70.3 wt. %, about 70.4 wt. %, about 70.5 wt. %, about 70.6 wt. %, about 70.7 wt. %, about 70.8 wt. %, about 70.9 wt. %, about 71 wt. %, about 71.1 wt. %, about 71.2 wt. %, about 71.3 wt. %, about 71.4 wt. %, about 71.5 wt. %, about 71.6 wt. %, about 71.7 wt. %, about 71.8 wt. %, about 71.9 wt. %, about 72 wt. %, about 72.1 wt. %, about 72.2 wt. %, about 72.3 wt. %, about 72.4 wt. %, about 72.5 wt. %, about 72.6 wt. %, about 72.7 wt. %, about 72.8 wt. %, about 72.9 wt. %, about 73 wt. %, about 73.1 wt. %, about 73.2 wt. %, about 73.3 wt. %, about 73.4 wt. %, about 73.5 wt. %, about 73.6 wt. %, about 73.7 wt. %, about 73.8 wt. %, about 73.9 wt. %, about 74 wt. %, about 74.1 wt. %, about 74.2 wt. %, about 74.3 wt. %, about 74.4 wt. %, about 74.5 wt. %, about 74.6 wt. %, about 74.7 wt. %, about 74.8 wt. %, about 74.9 wt. %, about 75 wt. %, about 75.1 wt. %, about 75.2 wt. %, about 75.3 wt. %, about 75.4 wt. %, about 75.5 wt. %, about 75.6 wt. %, about 75.7 wt. %, about 75.8 wt. %, about 75.9 wt. %, about 76 wt. %, about 76.1 wt. %, about 76.2 wt. %, about 76.3 wt. %, about 76.4 wt. %, about 76.5 wt. %, about 76.6 wt. %, about 76.7 wt. %, about 76.8 wt. %, about 76.9 wt. %, about 77 wt. %, about 77.1 wt. %, about 77.2 wt. %, about 77.3 wt. %, about 77.4 wt. %, about 77.5 wt. %, about 77.6 wt. %, about 77.7 wt. %, about 77.8 wt. %, about 77.9 wt. %, about 78 wt. %, about 78.1 wt. %, about 78.2 wt. %, about 78.3 wt. %, about 78.4 wt. %, about 78.5 wt. %, about 78.6 wt. %, about 78.7 wt. %, about 78.8 wt. %, about 78.9 wt. %, about 79 wt. %, about 79.1 wt. %, about 79.2 wt. %, about 79.3 wt. %, about 79.4 wt. %, about 79.5 wt. %, about 79.6 wt. %, about 79.7 wt. %, about 79.8 wt. %, about 79.9 wt. %, about 80 wt. %, about 80.1 wt. %, about 80.2 wt. %, about 80.3 wt. %, about 80.4 wt. %, about 80.5 wt. %, about 80.6 wt. %, about 80.7 wt. %, about 80.8 wt. %, about 80.9 wt. %, about 81 wt. %, about 81.1 wt. %, about 81.2 wt. %, about 81.3 wt. %, about 81.4 wt. %, about 81.5 wt. %, about 81.6 wt. %, about 81.7 wt. %, about 81.8 wt. %, about 81.9 wt. %, about 82 wt. %, about 82.1 wt. %, about 82.2 wt. %, about 82.3 wt. %, about 82.4 wt. %, about 82.5 wt. %, about 82.6 wt. %, about 82.7 wt. %, about 82.8 wt. %, about 82.9 wt. %, about 83 wt. %, about 83.1 wt. %, about 83.2 wt. %, about 83.3 wt. %, about 83.4 wt. %, about 83.5 wt. %, about 83.6 wt. %, about 83.7 wt. %, about 83.8 wt. %, about 83.9 wt. %, about 84 wt. %, about 84.1 wt. %, about 84.2 wt. %, about 84.3 wt. %, about 84.4 wt. %, about 84.5 wt. %, about 84.6 wt. %, about 84.7 wt. %, about 84.8 wt. %, about 84.9 wt. %, about 85 wt. %, about 85.1 wt. %, about 85.2 wt. %, about 85.3 wt. %, about 85.4 wt. %, about 85.5 wt. %, about 85.6 wt. %, about 85.7 wt. %, about 85.8 wt. %, about 85.9 wt. %, about 86 wt. %, about 86.1 wt. %, about 86.2 wt. %, about 86.3 wt. %, about 86.4 wt. %, about 86.5 wt. %, about 86.6 wt. %, about 86.7 wt. %, about 86.8 wt. %, about 86.9 wt. %, about 87 wt. %, about 87.1 wt. %, about 87.2 wt. %, about 87.3 wt. %, about 87.4 wt. %, about 87.5 wt. %, about 87.6 wt. %, about 87.7 wt. %, about 87.8 wt. %, about 87.9 wt. %, about 88 wt. %, about 88.1 wt. %, about 88.2 wt. %, about 88.3 wt. %, about 88.4 wt. %, about 88.5 wt. %, about 88.6 wt. %, about 88.7 wt. %, about 88.8 wt. %, about 88.9 wt. %, about 89 wt. %, about 89.1 wt. %, about 89.2 wt. %, about 89.3 wt. %, about 89.4 wt. %, about 89.5 wt. %, about 89.6 wt. %, about 89.7 wt. %, about 89.8 wt. %, about 89.9 wt. %, about 90 wt. %, about 90.1 wt. %, about 90.2 wt. %, about 90.3 wt. %, about 90.4 wt. %, about 90.5 wt. %, about 90.6 wt. %, about 90.7 wt. %, about 90.8 wt. %, about 90.9 wt. %, about 91 wt. %, about 91.1 wt. %, about 91.2 wt. %, about 91.3 wt. %, about 91.4 wt. %, about 91.5 wt. %, about 91.6 wt. %, about 91.7 wt. %, about 91.8 wt. %, about 91.9 wt. %, about 92 wt. %, about 92.1 wt. %, about 92.2 wt. %, about 92.3 wt. %, about 92.4 wt. %, about 92.5 wt. %, about 92.6 wt. %, about 92.7 wt. %, about 92.8 wt. %, about 92.9 wt. %, about 93 wt. %, about 93.1 wt. %, about 93.2 wt. %, about 93.3 wt. %, about 93.4 wt. %, about 93.5 wt. %, about 93.6 wt. %, about 93.7 wt. %, about 93.8 wt. %, about 93.9 wt. %, about 94 wt. %, about 94.1 wt. %, about 94.2 wt. %, about 94.3 wt. %, about 94.4 wt. %, about 94.5 wt. %, about 94.6 wt. %, about 94.7 wt. %, about 94.8 wt. %, about 94.9 wt. %, about 95 wt. %, about 95.1 wt. %, about 95.2 wt. %, about 95.3 wt. %, about 95.4 wt. %, about 95.5 wt. %, about 95.6 wt. %, about 95.7 wt. %, about 95.8 wt. %, about 95.9 wt. %, about 96 wt. %, about 96.1 wt. %, about 96.2 wt. %, about 96.3 wt. %, about 96.4 wt. %, about 96.5 wt. %, about 96.6 wt. %, about 96.7 wt. %, about 96.8 wt. %, about 96.9 wt. %, about 97 wt. %, about 97.1 wt. %, about 97.2 wt. %, about 97.3 wt. %, about 97.4 wt. %, about 97.5 wt. %, about 97.6 wt. %, about 97.7 wt. %, about 97.8 wt. %, about 97.9 wt. %, about 98 wt. %, about 98.1 wt. %, about 98.2 wt. %, about 98.3 wt. %, about 98.4 wt. %, about 98.5 wt. %, about 98.6 wt. %, about 98.7 wt. %, about 98.8 wt. %, about 98.9 wt. %, about 99 wt. %, about 99.1 wt. %, about 99.2 wt. %, about 99.3 wt. %, about 99.4 wt. %, about 99.5 wt. %, about 99.6 wt. %, about 99.7 wt. %, about 99.8 wt. %, about 99.9 wt. %, about 100 wt. %, about 100.1 wt. %, about 100.2 wt. %, about 100.3 wt. %, about 100.4 wt. %, about 100.5 wt. %, about 100.6 wt. %, about 100.7 wt. %, about 100.8 wt. %, about 100.9 wt. %, about 101 wt. %, about 101.1 wt. %, about 101.2 wt. %, about 101.3 wt. %, about 101.4 wt. %, about 101.5 wt. %, about 101.6 wt. %, about 101.7 wt. %, about 101.8 wt. %, about 101.9 wt. %, about 102 wt. %, about 102.1 wt. %, about 102.2 wt. %, about 102.3 wt. %, about 102.4 wt. %, about 102.5 wt. %, about 102.6 wt. %, about 102.7 wt. %, about 102.8 wt. %, about 102.9 wt. %, about 103 wt. %, about 103.1 wt. %, about 103.2 wt. %, about 103.3 wt. %, about 103.4 wt. %, about 103.5 wt. %, about 103.6 wt. %, about 103.7 wt. %, about 103.8 wt. %, about 103.9 wt. %, about 104 wt. %, about 104.1 wt. %, about 104.2 wt. %, about 104.3 wt. %, about 104.4 wt. %, about 104.5 wt. %, about 104.6 wt. %, about 104.7 wt. %, about 104.8 wt. %, about 104.9 wt. %, about 105 wt. %, about 105.1 wt. %, about 105.2 wt. %, about 105.3 wt. %, about 105.4 wt. %, about 105.5 wt. %, about 105.6 wt. %, about 105.7 wt. %, about 105.8 wt. %, about 105.9 wt. %, about 106 wt. %, about 106.1 wt. %, about 106.2 wt. %, about 106.3 wt. %, about 106.4 wt. %, about 106.5 wt. %, about 106.6 wt. %, about 106.7 wt. %, about 106.8 wt. %, about 106.9 wt. %, about 107 wt. %, about 107.1 wt. %, about 107.2 wt. %, about 107.3 wt. %, about 107.4 wt. %, about 107.5 wt. %, about 107.6 wt. %, about 107.7 wt. %, about 107.8 wt. %, about 107.9 wt. %, about 108 wt. %, about 108.1 wt. %, about 108.2 wt. %, about 108.3 wt. %, about 108.4 wt. %, about 108.5 wt. %, about 108.6 wt. %, about 108.7 wt. %, about 108.8 wt. %, about 108.9 wt. %, about 109 wt. %, about 109.1 wt. %, about 109.2 wt. %, about 109.3 wt. %, about 109.4 wt. %, about 109.5 wt. %, about 109.6 wt. %, about 109.7 wt. %, about 109.8 wt. %, about 109.9 wt. %, about 110 wt. %, about 110.1 wt. %, about 110.2 wt. %, about 110.3 wt. %, about 110.4 wt. %, about 110.5 wt. %, about 110.6 wt. %, about 110.7 wt. %, about 110.8 wt. %, about 110.9 wt. %, about 111 wt. %, about 111.1 wt. %, about 111.2 wt. %, about 111.3 wt. %, about 111.4 wt. %, about 111.5 wt. %, about 111.6 wt. %, about 111.7 wt. %, about 111.8 wt. %, about 111.9 wt. %, about 112 wt. %, about 112.1 wt. %, about 112.2 wt. %, about 112.3 wt. %, about 112.4 wt. %, about 112.5 wt. %, about 112.6 wt. %, about 112.7 wt. %, about 112.8 wt. %, about 112.9 wt. %, about 113 wt. %, about 113.1 wt. %, about 113.2 wt. %, about 113.3 wt. %, about 113.4 wt. %, about 113.5 wt. %, about 113.6 wt. %, about 113.7 wt. %, about 113.8 wt. %, about 113.9 wt. %, about 114 wt. %, about 114.1 wt. %, about 114.2 wt. %, about 114.3 wt. %, about 114.4 wt. %, about 114.5 wt. %, about 114.6 wt. %, about 114.7 wt. %, about 114.8 wt. %, about 114.9 wt. %, about 115 wt. %, about 115.1 wt. %, about 115.2 wt. %, about 115.3 wt. %, about 115.4 wt. %, about 115.5 wt. %, about 115.6 wt. %, about 115.7 wt. %, about 115.8 wt. %, about 115.9 wt. %, about 116 wt. %, about 116.1 wt. %, about 116.2 wt. %, about 116.3 wt. %, about 116.4 wt. %, about 116.5 wt. %, about 116.6 wt. %, about 116.7 wt. %, about 116.8 wt. %, about 116.9 wt. %, about 117 wt. %, about 117.1 wt. %, about 117.2 wt. %, about 117.3 wt. %, about 117.4 wt. %, about 117.5 wt. %, about 117.6 wt. %, about 117.7 wt. %, about 117.8 wt. %, about 117.9 wt. %, about 118 wt. %, about 118.1 wt. %, about 118.2 wt. %, about 118.3 wt. %, about 118.4 wt. %, about 118.5 wt. %, about 118.6 wt. %, about 118.7 wt. %, about 118.8 wt. %, about 118.9 wt. %, about 119 wt. %, about 119.1 wt. %, about 119.2 wt. %, about 119.3 wt. %, about 119.4 wt. %, about 119.5 wt. %, about 119.6 wt. %, about 119.7 wt. %, about 119.8 wt. %, about 119.9 wt. %, and about 120 wt. % of the polycyano compound of Formula (2).

In some embodiments, the process of making the polyamine of Formula (1) from the polycyano Formula (2) employs a reducing agent, a catalyst and a catalyst promoter. The term "catalyst promoter" as used herein includes any substances which themselves are not catalysts, but when mixed in small quantities with a catalyst increase the efficiency of the catalyst. In one embodiment, the catalyst promoter comprises one or more trace metals. In one embodiment, the catalyst promoter comprises one or more trace metals selected from the group consisting of Fe, Co, Mn, Mg, Al, Ni, Mo, Cu, Pd, and Pt. In one embodiment, the catalyst promoter comprises one or more trace metals selected from the group consisting of iron, chromium, molybdenum, and vanadium. In one embodiment, the combination of catalyst and catalyst promoter is provided as a single composition. In one embodiment, the combination of catalyst and catalyst promoter comprises Sponge Ni/Mo Catalyst and Fe/Cr as the promoter (e.g., A-4000 available from Johnson Matthey, West Depford, N.J., USA).

In an embodiment, the acid-labile polyamines of type Formula (1), may be further chemically modified prior to being incorporated into epoxy compositions.

In some embodiments, the process of making the polyamine of Formula (1) from the polycyano Formula (2) employs a suitable temperature condition. In one embodiment, the reduction is carried out at a temperature of from about 15° C. to about 200° C. In one embodiment, the reduction is carried out at a temperature of from about 20° C. to about 120° C. In one embodiment, the reduction is carried out at a temperature selected from the group consisting of about 15° C., about 25° C., about 35° C., about 45° C., about 55° C., about 65° C., about 75° C., about 85° C., about 95° C., about 100° C., about 100° C., about 105° C., about 115° C., about 125° C., about 135° C., about 145° C., about 155° C., about 165° C., about 175° C., about 185° C., about 195° C., and about 200° C. In one embodiment, the reduction is carried out at a temperature selected from the group consisting of about 15° C., less than about 25° C., less than about 35° C., less than about 45° C., less than about 55° C., less than about 65° C., less than about 75° C., less than about 85° C., less than about 95° C., less than about 100° C., less than about 100° C., less than about 105° C., less than about 115° C., less than about 125° C., less than about 135° C., less than about 145° C., less than about 155° C., less than about 165° C., less than about 175° C., less than about 185° C., less than about 195° C., and less than about 200° C.

In some embodiments, the reduction is carried out at a temperature selected from the group consisting of about 15° C. to about 120° C., about 15° C. to about 110° C., about 15° C. to about 100° C., about 15° C. to about 90° C., about 15° C. to about 80° C., about 15° C. to about 70° C., about 15° C. to about 60° C., about 15° C. to about 50° C., about 15° C. to about 40° C., about 20° C. to about 30° C., and about 20° C. to about 25° C.

In some embodiments, the process of making the polyamine of Formula (1) from the polycyano Formula (2) employs ammonia. In one embodiment, the reduction is carried out in the presence of anhydrous ammonia. In one embodiment, the reduction is carried out in the presence of aqueous ammonia. In one embodiment, the ammonia is recycled ammonia. In one embodiment, the reduction is carried out in the presence of ammonia in an amount of from about 1 mole to about 40 moles per mole of the compound of Formula (2) used. In one embodiment, the reduction is carried out in the presence of ammonia in an amount of about 2 moles, about 3 moles, about 4 moles, about 5 moles, about 10 moles, about 15 moles, about 20 moles, about 25 moles, about 30 moles, about 35 moles, or about 40 moles per mole of the compound of Formula (2) used.

In some embodiments, the process of making the polyamine of Formula (1) from the polycyano Formula (2) employs a solvent. Any suitable solvent may be used. In one embodiment, the reduction is carried out in the presence of a solvent selected from the group consisting of methanol, ethanol, tetrahydrofuran, dioxane and combinations thereof. In one embodiment, the solvent is recycled.

In some embodiments, the process of making the polyamine of Formula (1) from the polycyano Formula (2) is carried out in a batch reactor. In one embodiment, the reduction is carried out in a continuous reactor. In one embodiment, the reduction is carried out in continuous reactor selected from the group consisting of a flow reactor, a continuous stirred tank reactor, a trickle bed reactor, a fixed bed reactor, a loop reactor, a bubble reactor, a tube reactor, a pipe reactor, and a slurry reactor.

In some preferred embodiment, the reduction of the polycyano Formula (2) is carried out at a temperature of from about 20° C. to about 120° C. and at molecular hydrogen pressure of from about 80 psi to about 1500 psi. In some preferred embodiment, the reduction of the polycyano Formula (2) is carried out at a temperature of from about 20° C. to about 120° C. and at molecular hydrogen pressure of from about 100 psi to about 1500 psi. In some preferred embodiments, the reduction of the polycyano of Formula (2) is carried out at a temperature of from about 20° C. to about 80° C. and at molecular hydrogen pressure of from about 600 psi to about 1000 psi.

Exemplary polyamine compounds represented by Formula (1) include, but are not limited to, the following:

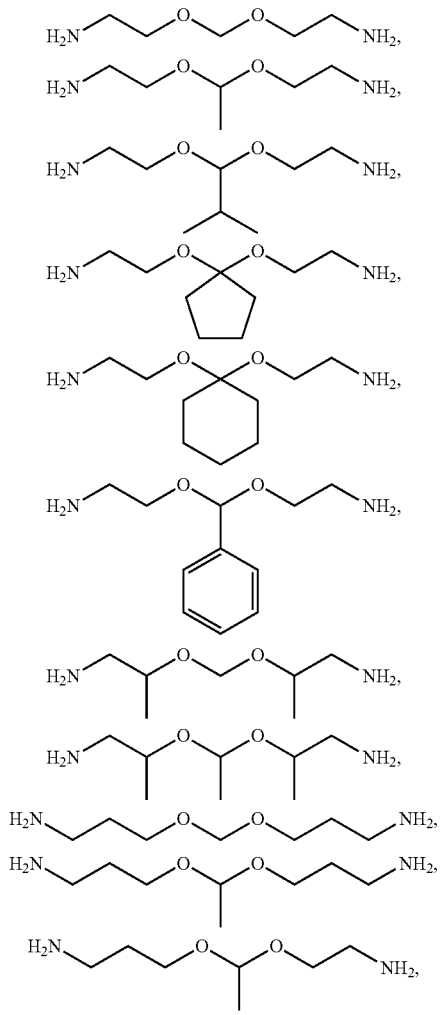

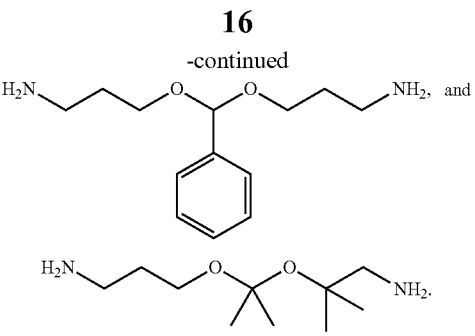

Exemplary polycyano compounds represented by Formula (2) include, but are not limited to, the following:

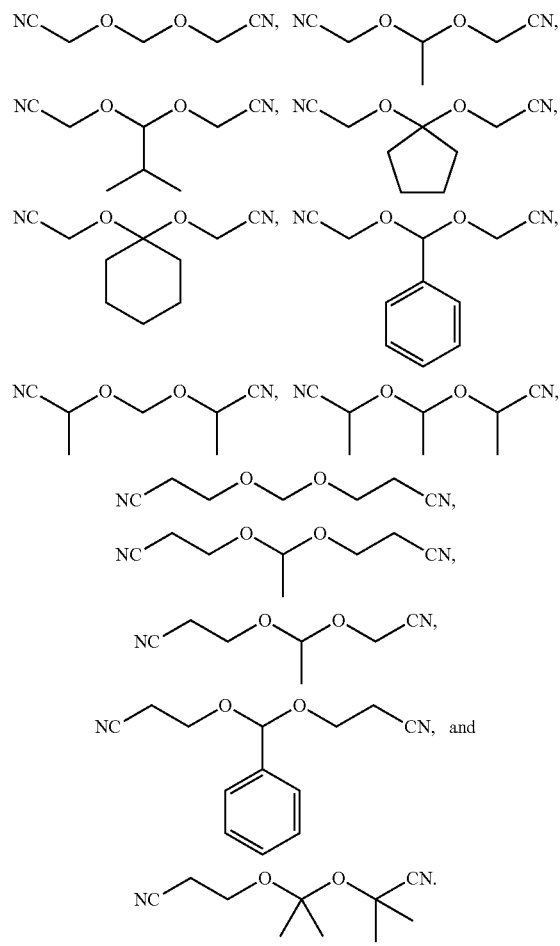

II. COMPOSITIONS AND METHOD OF USE

The present invention provides epoxy resin compositions for reinforced composite materials also well as for other epoxy applications, including coating, adhesives, and encapsulates. In some embodiments, the epoxy compositions are serviceable for both fiber-reinforced and non-fiber reinforced composite materials. In one embodiment, the epoxy resin composition comprises an epoxy resin; and a polyamine curing agent comprising a compound having Formula (1):

Formula (1)

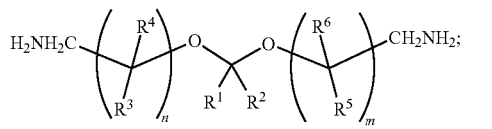

wherein: each of $R^1$ and $R^2$ is independently selected from the group consisting of hydrogen, alkyl group, cycloalkyl group and aromatic group; both of $R^1$ and $R^2$ can form a cyclic radical; each of $R^3$, $R^4$, $R^5$, and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 1 to 20.

In one embodiment, the epoxy resin composition comprises an epoxy resin that has an average of at least two epoxide groups per molecule. In one embodiment, the epoxy resin composition comprises a diepoxide resin. In one embodiment, the epoxy resin composition comprises a diepoxide resin selected from a group consisting of glycidyl ether epoxy resin, glycidyl ester epoxy resin, glycidyl amine epoxy resin, alicyclic epoxy resin, aliphatic epoxy resin, phenolic epoxy resin, and combinations thereof.

In some embodiments, the epoxy resin composition comprises an epoxy resin that comprises a blend of epoxy resins. In one embodiment, the epoxy resin composition comprises a blend of bisphenol-based epoxy resins. In one embodiment, the epoxy resin composition comprises a blend of bisphenol-based epoxy resins having an epoxide equivalent weight (EEW) in the range of 160 to 220. In one embodiment, the epoxy resin composition comprises a blend of bisphenol-based epoxy resins having an epoxide equivalent weight (EEW) in the range of 400 to 1500.

Generally, epoxy resin's epoxide equivalent weight (EEW) is defined by the following equation 1 (eq.1):

$$\text{Epoxy resing epoxide eq. wt. (or } EEW) = \frac{\text{MW of epoxy resin}}{\text{no. of epoxides in the epoxy resin}} \quad (\text{eq. 1})$$

wherein MW of epoxy resin represents molecular weight of the of epoxy resin.

Analogously, amine hydrogen equivalent weight is defined by the following equation 2 (eq.2):

$$\text{Amine hydrogen eq. wt. (or } AEW) = \frac{\text{MW of amine}}{\text{no. of active hydrogens}} \quad (\text{eq. 2})$$

wherein MW of amine represents molecular weight of the of the amine.

The stoichiometric ratio of an amine hardener to use with epoxy resin having a known or calculable epoxide equivalent weight EEW can be calculated using the following equation 3 (eq.3):

$$\text{stoichiometric ratio of amine} = \frac{\text{Amine H eq. wt.} \times 100}{\text{Epoxide eq. wt. of resin}} \quad (\text{eq. 3})$$

As, an example, EEW of bisphenol A diglycidyl ether (BPADGE), AEW of diamino acetal of Example 14 (diamino acetal C-14), and stoichiometric ratio of diamino acetal C-14 are calculated as follows.

Referring to FIG. 1, diamine acetal C-14 has a molecular weight of 129.24 atomic mass units (amu) and four active hydrogens. According to eq. 2, AEW of diamine acetal C-14 equals 32.31 (or 129.24÷4). BPADGE has a molecular weight of 340.41 amu and two epoxides. According to eq.1, EEW of BPADGE equals 170.205 (or 340.41÷2). According to eq.3, the stoichiometric ratio of diamine acetal C-14 to use with BPADGE equals 18.98 (or [32.31×100]÷170.205). In other words, if one wishes to use a stoichiometric amount of diamine acetal C-14 with BPADGE, one would need 18.98 parts diamine acetal C-14 by wt. per 100 parts resin (BPADGE) or 18.98 g of diamine acetal C-14 for every 100 g of BPADGE used.

In some embodiments, epoxy resins may be blended, filled, or modified with reactive and non-reactive components. In one such embodiment, it may be necessary to adjust the concentration of the curing polyamine agent to cure only the portion of the mix that is reactive; e.g., the resins and any reactive diluent present. In one embodiment, this may be done by calculating the epoxide equivalent weight (EEW) of the total mix and then applying equation 2 (eq. 2) to determine the amount of curing polyamine agent to add to 100 parts of the epoxy resin formulation. As an example, an EEW of a blended epoxy resins may be calculated according to equation 4 (eq.4).

$$EEW \text{ of mix} = \frac{\text{Total Wt. of Mix}}{\frac{Wta}{EEWa} + \frac{Wtb}{EEWb} + \ldots + \frac{Wtn}{EEWn}} \quad (\text{eq. 4})$$

wherein Total Wt. of Mix represents the molecular weight of the total mix and includes all materials, both reactive and non-reactive; a, b, . . . and n, are only the materials reactive with the polyamine curing agent and are characterised by an epoxy ring; EEWa represents EEW of reactive material a; EEWb represents EEW of reactive material b; and EEWn represents EEW of reactive material n.

In some embodiments of the present invention, the epoxy resin composition includes a blended epoxy resin, and a polyamine curing agent of Formula (1) as can be calculated by eq.3. In one embodiment, epoxy resin blend includes a mixture of a diglycidyl ether of a bisphenol, especially bisphenol A, having an EEW of 150-195, typically 180-190, and a diglycidyl ether of a bisphenol, especially bisphenol A having an EEW of 400-1500, preferably 1200-1400. In one embodiment, epoxy resin blend includes a mixture of a diglycidyl ether of a bisphenol, especially bisphenol A, having an EEW of 150-195, typically 180-190, a diglycidyl ether of a bisphenol, especially bisphenol A, having an EEW of 400-1500, preferably 1200-1400, and an epoxy phenolic novalac resin with a functionality of 2.2 to 4, typically 3.6 or above, having an EEW of 170-190, preferably 174-180. In one embodiment, epoxy resin blend includes a mixture of a diglycidyl ether of a bisphenol, especially bisphenol A, having an EEW of 150-195, typically 176, a diglycidyl ether of a bisphenol, typically bisphenol A, having an EEW of 400-1500, preferably 1200-1400, and a tetra-functional epoxy having an EEW of 117-134.

Various bisphenol-based epoxy resins may be used for the present invention. In particular, in one embodiment the bisphenol-based epoxy resin is an intermediate molecule based on the reaction of epichlorohydrin and bisphenol A ("BPA") and/or bisphenol F ("BPF"). Bisphenol-based epoxy resins that are useful for the present invention include, but are not limited to, bisphenol A diglycidyl ether, ("BPADGE") and its oligomers and bisphenol F diglycidyl ether, ("BPFDGE") and its oligomers. FIG. 4 depicts various epoxy resins including generic structures for BPADGE and BPFDGE and their oligomers. In some embodiments, molecular weight of preferred oligomers of BPADGE and BPFDGE can be up to approximately 6000 g/mol. In one embodiment, the bisphenol-based epoxy resin based on bisphenol A has a molecular weight in the range of about 340 to about 6000 g/mol. In one embodiment, the bisphenol-based epoxy resin based on bisphenol F has a molecular weight in the range of about 310 to about 6000 g/mol. In some embodiments, the bisphenol-based epoxy resins have a molecular weight between and optionally including any two of the following values: 298, 300, 310, 340, 400, 600, 800, 1000, 1200, 1500, 1800, 2100, 2400, 2700, 3000, 3300, 3600, 3900, 4200, 4500, 4800, 5100, 5400, and 6000. Since the bisphenol-based epoxy resins have 2 epoxy groups per oligomer, the bisphenol-based epoxy resins have an epoxide equivalent weight (EEW) that is generally about half of the molecular weight of the oligomer. In one embodiment, the bisphenol-based epoxy resin is present from about 40 to about 95 wt %, based on the combined weight of the bisphenol-based epoxy resin, amine curing agent, and multi-epoxy reactive diluent. In another embodiment, the bisphenol-based epoxy resin is present from about 40 to about 95 wt %, based on the combined weight of the components in the curable composition. In some embodiments, the bisphenol-based epoxy resin is present in an amount between and optionally including any two of the following values: 40, 45, 50, 55, 60, 65, 70, 75, 80, 85, 90, and 95 wt %, based on the combined weight of the components in the curable composition.

Examples of commercially available bisphenol A diglycidyl ether epoxy resins are Insulcast 503/504 BLK; Insulcast 504 Clear; Insulcast 125; Insulcast 333; Insulcast 136; and Insulcast 502, available (from ITW Polymer Technologies (Glenview, Ill., U.S.A.); Epon 828, and Epon 826 available from Hexion Specialty Chemicals, Inc., now Momentive Specialty Chemicals, Inc., part of Momentive Performance Materials Holdings, Inc., (Columbus, Ohio, U.S.A.). Examples of commercially available bisphenol F diglycidyl ether epoxy resins are Araldite® GY285, Araldite® GY281, and Araldite® PY302-2 from Huntsman International, LLC (Salt Lake City, Utah, USA). Mixtures of bisphenol-based epoxy resins can be used in the curable composition.

In some embodiments, less than stoichiometric amount of polyamine curing agent of Formula (1) is used in the epoxy resin composition in accordance with the present invention. In one embodiment, the epoxy resin composition contains 2% of the stoichiometric amount of polyamine curing agent of Formula (1). In one embodiment, the epoxy resin composition contains the polyamine curing agent of Formula (1) in a percentage selected from the group consisting of about 4%, about 6%, about 8%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, and about 98% of the stoichiometric amount of polyamine curing agent of Formula (1). In one embodiment, the epoxy resin composition contains the polyamine curing agent of Formula (1) in a percentage selected from the group consisting of less than about 4% but greater than about 2%, less than about 6% but greater than about 2%, less than about 8% but greater than about 2%, less than about 10% but greater than about 2%, less than about 12% but greater than about 2%, less than about 14% but greater than about 2%, less than about 16% but greater than about 2%, less than about 18% but greater than about 2%, less than about 20% but greater than about 2%, less than about 22% but greater than about 2%, less than about 24% but greater than about 2%, less than about 26% but greater than about 2%, less than about 28% but greater than about 2%, less than about 30% but greater than about 2%, less than about 32% but greater than about 2%, less than about 34% but greater than about 2%, less than about 36% but greater than about 2%, less than about 38% but greater than about 2%, less than about 40% but greater than about 2%, less than about 42% but greater than about 2%, less than about 44% but greater than about 2%, less than about 46% but greater than about 2%, less than about 48% but greater than about 2%, less than about 50% but greater than about 2%, less than about 52% but greater than about 2%, less than about 54% but greater than about 2%, less than about 56% but greater than about 2%, less than about 58% but greater than about 2%, less than about 60% but greater than about 2%, less than about 62% but greater than about 2%, less than about 64% but greater than about 2%, less than about 66% but greater than about 2%, less than about 68% but greater than about 2%, less than about 70% but greater than about 2%, less than about 72% but greater than about 2%, less than about 74% but greater than about 2%, less than about 76% but greater than about 2%, less than about 78% but greater than about 2%, less than about 80% but greater than about 2%, less than about 82% but greater than about 2%, less than about 84% but greater than about 2%, less than about 86% but greater than about 2%, less than about 88% but greater than about 2%, less than about 90% but greater than about 2%, less than about 92% but greater than about 2%, less than about 94% but greater than about 2%, less than about 96% but greater than about 2%, and less than about 98% but greater than about 2% of the stoichiometric amount of polyamine curing agent of Formula (1).

Unless otherwise stated herein the terms "hardener", "curing agent", "cross-linking agent" are used interchangeable as synonyms of "cross-linking agent". As is the case with thermosetting epoxies, the processing properties (e.g. curing time, peak exotherm, mixed viscosity, etc.) and cured resin physical properties (Tg, tensile strength, flexibility modulus, chemical resistance, conductivity, adhesion, color, impact strength, etc.) can be modified by the addition of auxiliary materials to the base epoxy resin/hardener composition for the purposes of preparation of epoxy formulations tailored for a given application. Accordingly, in some embodiments, the epoxy resin composition further includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, gloss additive and combinations thereof.

In some embodiments, amino molecules that contain 2, or less than 2, active N—H hydrogens can be used in combination with the polyamine curing agents of Formula (1). Primary monoamines, bis(secondary) diamine molecules, and other molecules that contain only two active N—H hydrogens are suitable for use in the epoxy resin composition of the present invention as chain extenders. In one embodiment, the chain extenders are used to adjust the cross-link density of a cured epoxy resin in accordance with exemplary embodiments of the present invention. By adding these chain extenders to the polyamine curing agents of Formula (1) one can decrease the cross-linking density in the final cured epoxy matrix. In an embodiment, specific, but non-limiting, examples of molecules that contain only two active N—H hydrogens include monoethanolamine, 3-aminopropanol, 2-aminopropanol, benzylamine, aniline, p-anisidine, butylamine, piperazine, and N,N'-dimethylethylenediamine, tert-butylamine, and, sec-butylamine. In an embodiment, the epoxy resin composition of the present invention includes at least one amine chain extender in an amount ranging from about 0% to about 98% relative to weight of the polyamine curing agent of Formula (1).

In some embodiments, conventional, non-labile polyamino molecules that contain greater than 2 N—H hydrogens are used in combination with polyamine curing agents of Formula (1). Chain extenders can be combined with the polyamine curing agent of Formula (1) to increase the amount of nondegradable cross-links in the final cured epoxy matrix. In one embodiment, chain extenders in an amount of from about 5 wt. % to 25 wt. % is combined with the polyamine curing agent of Formula (1) to increase the amount of nondegradable cross-links in the final cured epoxy matrix. In one embodiment, chain extenders in an amount selected from the group consisting of about 5 wt. % to about 25 wt. %, about 6 wt. % to about 25, about 7 wt. % to about 25, about 8 wt. % to about 25 wt. %, about 9 wt. % to about 25 wt. %, about 10 wt. % to about 25 wt. %, about 11 wt. % to about 25 wt. %, about 12 wt. % to about 25 wt. %, about 13 wt. % to about 25 wt. %, about 14 wt. % to about 25 wt. %, about 15 wt. % to about 25 wt. %, about 16 wt. % to about 25 wt. %, about 17 wt. % to about 25 wt. %, about 18 wt. % to about 25 wt. %, about 19 wt. % to about 25 wt. %, about 20 wt. % to about 25 wt. %, about 21 wt. % to about 25 wt. %, about 22 wt. % to about 25 wt. %, about 23 wt. % to about 25 wt. %, and about 24 wt. % to about 25 is combined with the polyamine curing agent of Formula (1) to increase the amount of nondegradable cross-links in the final cured epoxy matrix.

In some embodiments, the epoxy resin composition further includes a reinforcing agent. In one embodiment, reinforcing agent is selected from a group consisting of glass fiber, carbon fiber, natural fiber, and chemical fiber, and the non-fibrous material is at least one selected from a group consisting of carbon nanotube, carbon black, metal nanoparticle, organic nanoparticle, iron oxide, boron nitride, and combinations thereof.

In another aspect, the present invention provides a method of curing an epoxy resin formulation in accordance with the present invention. In one embodiment, the method comprises heating an epoxy resin composition of the present invention to form a cured epoxy resin composition. In one embodiment, the epoxy resin composition is cured to a curing degree of at least 25% cure. In one embodiment, the epoxy resin composition is cured to a curing degree of at least 35% cure. In one embodiment, the epoxy resin composition is cured to a curing degree of at least 45% cure. In one embodiment, the epoxy resin composition is cured to a curing degree of at least 55% cure. In one embodiment, the epoxy resin composition is cured to a curing degree selected from the group consisting of at least 65% cure, at least 75% cure, at least 85% cure, and at least 95% cure.

In some embodiments, the method of curing an epoxy resin formulation in accordance with the present invention is used to produce reinforced composite. In one embodiment, the method of curing an epoxy resin formulation in accordance with the present invention produces a composite reinforced with a reinforcing component selected from the group consisting of glass fibers, aramid fibers, graphite fibers, carbon fibers, natural fibers, non-natural fibers and combinations thereof.

In another aspect, the present invention provides a cross-linked polymer matrix, wherein the cross-linked polymer is derived from an epoxy resin having at least two epoxide and a cross-linking group derived from a polyamine curing agent represented by Formula (1):

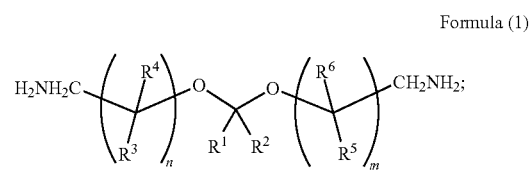

Formula (1)

wherein: each of $R^1$ and $R^2$ is independently selected from the group consisting of hydrogen, alkyl group, cycloalkyl group and aromatic group; or both of $R^1$ and $R^2$ forms a cyclic radical; each of $R^3$, $R^4$, $R^5$ and $R^6$ is independently selected from the group consisting of hydrogen, alkyl group, cycloalkyl group and aromatic group; $R^3$ and $R^4$ can combine with each other to form a cyclic radical; $R^5$ and $R^6$ can combine with each other to form a cyclic radical; and each m and n is independently an integer ranging from 1 to 20. In one embodiment, cross-linked polymer matrix is derived from a diepoxide epoxy resin and a cross-linking group derived from a polyamine curing agent represented by Formula (1). In one embodiment, the cross-linked polymer matrix is reinforced with a reinforcing agent derived from a reinforcing component selected from the group consisting of glass fibers, aramid fibers, graphite fibers, carbon fibers, natural fibers, non-natural fibers and combinations thereof. In one embodiment, the cross-linked polymer matrix is a cross-linked epoxy resin, wherein the epoxy resin is selected from the group consisting of glycidyl ether epoxy resin, glycidyl ester epoxy resin, glycidyl amine epoxy resin, alicyclic epoxy resin, aliphatic epoxy resin, and phenolic epoxy resin. In one embodiment, the cross-linked polymer matrix is reinforced with the reinforcement material selected from the group consisting of a fibrous material and a non-fibrous material. In one embodiment, the cross-linked polymer matrix is reinforced with a fibrous material selected from a group consisting of glass fiber, carbon fiber, natural fiber, and chemical fiber. In one embodiment, the cross-linked polymer matrix is reinforced with a non-fibrous material selected from the group consisting of carbon nanotube, carbon black, metal nanoparticle, organic nanoparticle, iron oxide, and boron nitride. In one embodiment, the reinforced cross-linked polymer matrix includes an auxiliary material selected from the group consisting of accelerator, diluents, toughening agent, thickening agent, adhesion promoter, optical brightener, pigment, adducting component, coupling agent, filler, decorative component, thixotropic agent, fluorophore, UV-absorber, anti-oxidant, monoamine, and gloss additive. In some embodiments, the reinforced cross-linked polymer matrix is prepared by at least one method selected from the group consisting of wet lay-up, vacuum infusion, filament winding, and resin transfer molding, prepreg, and compression molding.

In another aspect, the present invention provides a method for recycling a cross-linked polymer matrix in accordance with the present invention. FIG. 4 shows a non-limiting example of the method for recycling a cross-linked polymer matrix in accordance with the present invention. In one embodiment, the method for recycling the cross-linked polymer matrix comprises degrading the cross-linked polymer matrix with an acid in the presence of a solvent. In one embodiment, degrading the cross-linked matrix with an acid in the presence of a solvent is performed under a heating condition. In one embodiment, the cross-linked polymer matrix is degraded with an acid selected from a group consisting of hydrochloric acid, acetic acid, lactic acid, formic acid, propionic acid, citric acid, methane sulfonic acid, p-toluene sulfonic acid, sulfuric acid, benzoic acid, and phthalic acid. In one embodiment, the cross-linked polymer matrix is degraded with an acid in the presence of a solvent selected from the group consisting of methanol, ethanol, ethylene glycol, isopropyl alcohol, butyl alcohol, pentanol, hexanol, heptanol, octanol alcohol, nonyl alcohol, water, and combinations thereof. In one embodiment, the cross-linked polymer matrix is degraded with an acid in an amount ranging from about 2% to 90% by weight of the cross-linked polymer matrix. In one embodiment, the cross-linked polymer matrix is degrated with an acid in an amount selected from about 2 wt. % to about 90 wt. %, about 3 wt. % to about 90 wt. %, about 4 wt. % to about 90 wt. %, about 5 wt. % to about 90 wt. %, about 6 wt. % to about 90 wt. %, about 7 wt. % to about 90 wt. %, about 8 wt. % to about 90 wt. %, about 9 wt. % to about 90 wt. %, about 10 wt. % to about 90 wt. %, about 11 wt. % to about 90 wt. %, about 12 wt. % to about 90 wt. %, about 13 wt. % to about 90 wt. %, about 14 wt. % to about 90 wt. %, about 15 wt. % to about 90 wt. %, about 16 wt. % to about 90 wt. %, about 17 wt. % to about 90 wt. %, about 18 wt. % to about 90 wt. %, about 19 wt. % to about 90 wt. %, about 20 wt. % to about 90 wt. %, about 21 wt. % to about 90 wt. %, about 22 wt. % to about 90 wt. %, about 23 wt. % to about 90 wt. %, about 24 wt. % to about 90 wt. %, about 25 wt. % to about 90 wt. %, about 26 wt. % to about 90 wt. %, about 27 wt. % to about 90 wt. %, about 28 wt. % to about 90 wt. %, about 29 wt. % to about 90 wt. %, about 30 wt. % to about 90 wt. %, about 31 wt. % to about 90 wt. %, about 32 wt. % to about 90 wt. %, about 33 wt. % to about 90 wt. %, about 34 wt. % to about 90 wt. %, about 35 wt. % to about 90 wt. %, about 36 wt. % to about 90 wt. %, about 37 wt. % to about 90 wt. %, about 38 wt. % to about 90 wt. %, about 39 wt. % to about 90 wt. %, about 40 wt. % to about 90 wt. %, about 41 wt. % to about 90 wt. %, about 42 wt. % to about 90 wt. %, about 43 wt. % to about 90 wt. %, about 44 wt. % to about 90 wt. %, about 45 wt. % to about 90 wt. %, about 46 wt. % to about 90 wt. %, about 47 wt. % to about 90 wt. %, about 48 wt. % to about 90 wt. %, about 49 wt. % to about 90 wt. %, about 50 wt. % to about 90 wt. %, about 51 wt. % to about 90 wt. %, about 52 wt. % to about 90 wt. %, about 53 wt. % to about 90 wt. %, about 54 wt. % to about 90 wt. %, about 55 wt. % to about 90 wt. %, about 56 wt. % to about 90 wt. %, about 57 wt. % to about 90 wt. %, about 58 wt. % to about 90 wt. %, about 59 wt. % to about 90 wt. %, about 60 wt. % to about 90 wt. %, about 61 wt. % to about 90 wt. %, about 62 wt. % to about 90 wt. %, about 63 wt. % to about 90 wt. %, about 64 wt. % to about 90 wt. %, about 65 wt. % to about 90 wt. %, about 66 wt. % to about 90 wt. %, about 67 wt. % to about 90 wt. %, about 68 wt. % to about 90 wt. %, about 69 wt. % to about 90 wt. %, about 70 wt. % to about 90 wt. %, about 71 wt. % to about 90 wt. %, about 72 wt. % to about 90 wt. %, about 73 wt. % to about 90 wt. %, about 74 wt. % to about 90 wt. %, about 75 wt. % to about 90 wt. %, about 76 wt. % to about 90 wt. %, about 77 wt. % to about 90 wt. %, about 78 wt. % to about 90 wt. %, about 79 wt. % to about 90 wt. %, about 80 wt. % to about 90 wt. %, about 81 wt. % to about 90 wt. %, about 82 wt. % to about 90 wt. %, about 83 wt. % to about 90 wt. %, about 84 wt. % to about 90 wt. %, about 85 wt. % to about 90 wt. %, about 86 wt. % to about 90 wt. %, about 87 wt. % to about 90 wt. %, about 88 wt. % to about 90 wt. %, and about 89 wt. % to about 90 wt. % of the cross-linked polymer matrix.

In one embodiment, the cross-linked polymer matrix is degraded with an acid in an amount selected from the group consisting of about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 13 wt. %, about 14 wt. %, about 15 wt. %, about 16 wt. %, about 17 wt. %, about 18 wt. %, about 19 wt. %, about 20 wt. %, about 21 wt. %, about 22 wt. %, about 23 wt. %, about 24 wt. %, about 25 wt. %, about 26 wt. %, about 27 wt. %, about 28 wt. %, about 29 wt. %, about 30 wt. %, about 31 wt. %, about 32 wt. %, about 33 wt. %, about 34 wt. %, about 35 wt. %, about 36 wt. %, about 37 wt. %, about 38 wt. %, about 39 wt. %, about 40 wt. %, about 41 wt. %, about 42 wt. %, about 43 wt. %, about 44 wt. %, about 45 wt. %, about 46 wt. %, about 47 wt. %, about 48 wt. %, about 49 wt. %, about 50 wt. %, about 51 wt. %, about 52 wt. %, about 53 wt. %, about 54 wt. %, about 55 wt. %, about 56 wt. %, about 57 wt. %, about 58 wt. %, about 59 wt. %, about 60 wt. %, about 61 wt. %, about 62 wt. %, about 63 wt. %, about 64 wt. %, about 65 wt. %, about 66 wt. %, about 67 wt. %, about 68 wt. %, about 69 wt. %, about 70 wt. %, about 71 wt. %, about 72 wt. %, about 73 wt. %, about 74 wt. %, about 75 wt. %, about 76 wt. %, about 77 wt. %, about 78 wt. %, about 79 wt. %, about 80 wt. %, about 81 wt. %, about 82 wt. %, about 83 wt. %, about 84 wt. %, about 85 wt. %, about 86 wt. %, about 87 wt. %, about 88 wt. %, about 89 wt. %, and about 90 wt. %.

In some embodiments, the method for recycling a cross-linked polymer matrix in accordance with the present invention is carried out under a heating condition. In one embodiment, the cross-linked polymer matrix is degraded at a temperature ranging from 15° C. to 400° C. In one embodiment, the cross-linked polymer matrix is degraded at a temperature ranging from 60° C. to 120° C. In one embodiment, the cross-linked polymer matrix is degraded at a temperature selected from the group consisting of about 60° C. to about 120° C., about 61° C. to about 120° C., about 62° C. to about 120° C., about 63° C. to about 120° C., about 64° C. to about 120° C., about 65° C. to about 120° C., about 66° C. to about 120° C., about 67° C. to about 120° C., about 68° C. to about 120° C., about 69° C. to about 120° C., about 70° C. to about 120° C., about 71° C. to about 120° C., about 72° C. to about 120° C., about 73° C. to about 120° C., about 74° C. to about 120° C., about 75° C. to about 120° C., about 76° C. to about 120° C., about 77° C. to about 120° C., about 78° C. to about 120° C., about 79° C. to about 120° C., about 80° C. to about 120° C., about 81° C. to about 120° C., about 82° C. to about 120° C., about 83° C. to about 120° C., about 84° C. to about 120° C., about 85° C. to about 120° C., about 86° C. to about 120° C., about 87° C. to about 120° C., about 88° C. to about 120° C., about 89° C. to about 120° C., about 90° C. to about 120° C., about 91° C. to about 120° C., about 92° C. to about 120° C., about 93° C. to about 120° C., about 94° C. to about 120° C., about 95° C. to about 120° C., about 96°

C. to about 120° C., about 97° C. to about 120° C., about 98° C. to about 120° C., about 99° C. to about 120° C., about 100° C. to about 120° C., about 101° C. to about 120° C., about 102° C. to about 120° C., about 103° C. to about 120° C., about 104° C. to about 120° C., about 105° C. to about 120° C., about 106° C. to about 120° C., about 107° C. to about 120° C., about 108° C. to about 120° C., about 109° C. to about 120° C., about 110° C. to about 120° C., about 111° C. to about 120° C., about 112° C. to about 120° C., about 113° C. to about 120° C., about 114° C. to about 120° C., about 115° C. to about 120° C., about 116° C. to about 120° C., about 117° C. to about 120° C., about 118° C. to about 120° C., and about 119° C. to about 120° C.

In one embodiment, the cross-linked polymer matrix is degraded at a temperature selected from the group consisting of about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., about 116° C., about 117° C., about 118° C., about 119° C., and about 120° C.

In some embodiments, the cross-linked polymer matrix is degraded at a temperature ranging from 20° C. to 400° C. In one embodiment, the cross-linked polymer matrix is degraded at a temperature selected from the group consisting of about 20° C. to about 400° C., about 25° C. to about 400° C., about 30° C. to about 400° C., about 35° C. to about 400° C., about 40° C. to about 400° C., about 45° C. to about 400° C., about 50° C. to about 400° C., about 55° C. to about 400° C., about 60° C. to about 400° C., about 65° C. to about 400° C., about 70° C. to about 400° C., about 75° C. to about 400° C., about 80° C. to about 400° C., about 85° C. to about 400° C., about 90° C. to about 400° C., about 95° C. to about 400° C., about 100° C. to about 400° C., about 105° C. to about 400° C., about 110° C. to about 400° C., about 115° C. to about 400° C., about 120° C. to about 400° C., about 125° C. to about 400° C., about 130° C. to about 400° C., about 135° C. to about 400° C., about 140° C. to about 400° C., about 145° C. to about 400° C., about 150° C. to about 400° C., about 155° C. to about 400° C., about 160° C. to about 400° C., about 165° C. to about 400° C., about 170° C. to about 400° C., about 175° C. to about 400° C., about 180° C. to about 400° C., about 185° C. to about 400° C., about 190° C. to about 400° C., about 195° C. to about 400° C., about 200° C. to about 400° C., about 205° C. to about 400° C., about 210° C. to about 400° C., about 215° C. to about 400° C., about 220° C. to about 400° C., about 225° C. to about 400° C., about 230° C. to about 400° C., about 235° C. to about 400° C., about 240° C. to about 400° C., about 245° C. to about 400° C., about 250° C. to about 400° C., about 255° C. to about 400° C., about 260° C. to about 400° C., about 265° C. to about 400° C., about 270° C. to about 400° C., about 275° C. to about 400° C., about 280° C. to about 400° C., about 285° C. to about 400° C., about 290° C. to about 400° C., about 295° C. to about 400° C., about 300° C. to about 400° C., about 305° C. to about 400° C., about 310° C. to about 400° C., about 315° C. to about 400° C., about 320° C. to about 400° C., about 325° C. to about 400° C., about 330° C. to about 400° C., about 335° C. to about 400° C., about 340° C. to about 400° C., about 345° C. to about 400° C., about 350° C. to about 400° C., about 355° C. to about 400° C., about 360° C. to about 400° C., about 365° C. to about 400° C., about 370° C. to about 400° C., about 375° C. to about 400° C., about 380° C. to about 400° C., about 385° C. to about 400° C., about 390° C. to about 400° C., and about 395° C. to about 400° C.

In some embodiments, the cross-linked polymer matrix is degraded at a temperature selected from the group consisting of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., about 295° C., about 300° C., about 305° C., about 310° C., about 315° C., about 320° C., about 325° C., about 330° C., about 335° C., about 340° C., about 345° C., about 350° C., about 355° C., about 360° C., about 365° C., about 370° C., about 375° C., about 380° C., about 385° C., about 390° C., about 395° C., and about 400° C.

In some embodiments, the cross-linked polymer matrix is degraded by heating the cross-linked polymer matrix with an acid at a temperature selected from the group consisting of less than about 400° C. but greater than about 10° C., less than about 395° C. but greater than about 10° C., less than about 390° C. but greater than about 10° C., less than about 385° C. but greater than about 10° C., less than about 380° C. but greater than about 10° C., less than about 375° C. but greater than about 10° C., less than about 370° C. but greater than about 10° C., less than about 365° C. but greater than about 10° C., less than about 360° C. but greater than about 10° C., less than about 355° C. but greater than about 10° C., less than about 350° C. but greater than about 10° C., less than about 345° C. but greater than about 10° C., less than about 340° C. but greater than about 10° C., less than about 335° C. but greater than about 10° C., less than about 330° C. but greater than about 10° C., less than about 325° C. but greater than about 10° C., less than about 320° C. but greater than about 10° C., less than about 315° C. but greater than about 10° C., less than about 32° C. but greater than about 10° C., less than about 305° C. but greater than about 10° C., less than about 300° C. but greater than about 10° C., less than about 295° C. but greater than about 10° C., less than about 290° C. but greater than about 10° C., less than about 285° C. but greater than about 10° C., less than about 280° C. but greater than about 10° C., less than about 275° C. but greater than about 10° C., less than about 270° C. but greater than about 10° C., less than about 265° C. but greater than about 10° C., less than about 260° C. but greater than about 10° C., less than about 255° C. but greater than about 10° C., less than about 250° C. but greater than about 10° C., less than about 245° C. but greater than about 10° C., less than about 240° C. but greater than about 10° C., less than about 235° C. but greater than about 10° C., less than about 230° C. but greater than about 10° C., less than about 225° C. but greater than about 10° C., less than about 220° C. but greater than about 10° C., less than about 215° C. but greater than about 10° C., less than about 22° C. but greater than about 10° C., less than about 205° C. but greater than about 10° C., less than about 200° C. but greater than about 10° C., less than about 195° C. but greater than about 10° C., less than about 190° C. but greater than about 10° C., less than about 185° C. but greater than about 10° C., less than about 180° C. but greater than about 10° C., less than about 175° C. but greater than about 10° C., less than about 170° C. but greater than about 10° C., less than about 165° C. but greater than about 10° C., less than about 160° C. but greater than about 10° C., less than about 155° C. but greater than about 10° C., less than about 150° C. but greater than about 10° C., less than about 145° C. but greater than about 10° C., less than about 140° C. but greater than about 10° C., less than about 135° C. but greater than about 10° C., less than about 130° C. but greater than about 10° C., less than about 125° C. but greater than about 10° C., less than about 120° C. but greater than about 10° C., less than about 115° C. but greater than about 10° C., less than about 12° C. but greater than about 10° C., less than about 105° C. but greater than about 10° C., less than about 100° C. but greater than about 10° C., less than about 95° C. but greater than about 10° C., less than about 90° C. but greater than about 10° C., less than about 85° C. but greater than about 10° C., less than about 80° C. but greater than about 10° C., less than about 75° C. but greater than about 10° C., less than about 70° C. but greater than about 10° C., less than about 65° C. but greater than about 10° C., less than about 60° C. but greater than about 10° C., less than about 55° C. but greater than about 10° C., less than about 50° C. but greater than about 10° C., less than about 45° C. but greater than about 10° C., less than about 40° C. but greater than about 10° C., less than about 35° C. but greater than about 10° C., less than about 30° C. but greater than about 10° C., less than about 25° C. but greater than about 10° C., less than about 20° C. but greater than about 10° C., and less than about 15° C. but greater than about 10° C.

In some embodiments, the cross-linked polymer matrix is degraded by heating the cross-linked polymer matrix with an acid for a time of from about 1 hour to about 48 hours. In some embodiments, the cross-linked polymer matrix is degraded by heating the cross-linked polymer matrix with an acid for a time of from about 1 hour to 12 hours.

In some embodiments, the cross-linked polymer matrix is degraded by heating the cross-linked polymer matrix with an acid for a time selected from the group consisting of about 1 hour to about 48 hours, about 2 hours to about 48 hours, about 3 hours to about 48 hours, about 4 hours to about 48 hours, about 5 hours to about 48 hours, about 6 hours to about 48 hours, about 7 hours to about 48 hours, about 8 hours to about 48 hours, about 9 hours to about 48 hours, about 10 hours to about 48 hours, about 11 hours to about 48 hours, about 12 hours to about 48 hours, about 13 hours to about 48 hours, about 14 hours to about 48 hours, about 15 hours to about 48 hours, about 16 hours to about 48 hours, about 17 hours to about 48 hours, about 18 hours to about 48 hours, about 19 hours to about 48 hours, about 20 hours to about 48 hours, about 21 hours to about 48 hours, about 22 hours to about 48 hours, about 23 hours to about 48 hours, about 24 hours to about 48 hours, about 25 hours to about 48 hours, about 26 hours to about 48 hours, about 27 hours to about 48 hours, about 28 hours to about 48 hours, about 29 hours to about 48 hours, about 30 hours to about 48 hours, about 31 hours to about 48 hours, about 32 hours to about 48 hours, about 33 hours to about 48 hours, about 34 hours to about 48 hours, about 35 hours to about 48 hours, about 36 hours to about 48 hours, about 37 hours to about 48 hours, about 38 hours to about 48 hours, about 39 hours to about 48 hours, about 40 hours to about 48 hours, about 41 hours to about 48 hours, about 42 hours to about 48 hours, about 43 hours to about 48 hours, about 44 hours to about 48 hours, about 45 hours to about 48 hours, about 46 hours to about 48 hours, and about 47 hours to about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 1 hour, less than about 46 hours but greater than about 1 hour, less than about 45 hours but greater than about 1 hour, less than about 44 hours but greater than about 1 hour, less than about 43 hours but greater than about 1 hour, less than about 42 hours but greater than about 1 hour, less than about 41 hours but greater than about 1 hour, less than about 40 hours but greater than about 1 hour, less than about 39 hours but greater than about 1 hour, less than about 38 hours but greater than about 1 hour, less than about 37 hours but greater than about 1 hour, less than about 36 hours but greater than about 1 hour, less than about 35 hours but greater than about 1 hour, less than about 34 hours but greater than about 1 hour, less than about 33 hours but greater than about 1 hour, less than about 32 hours but greater than about 1 hour, less than about 31 hours but greater than about 1 hour, less than about 30 hours but greater than about 1 hour, less than about 29 hours but greater than about 1 hour, less than about 28 hours but greater than about 1 hour, less than about 27 hours but greater than about 1 hour, less than about 26 hours but greater than about 1 hour, less than about 25 hours but greater than about 1 hour, less than about 24 hours but greater than about 1 hour, less than about 23 hours but greater than about 1 hour, less than about 22 hours but greater than about 1 hour, less than about 21 hours but greater than about 1 hour, less than about 20 hours but greater than about 1 hour, less than about 19 hours but greater than about 1 hour, less than about 18 hours but greater than about 1 hour, less than about 17 hours but greater than about 1 hour, less than about 16 hours but greater than about 1 hour, less than about 15 hours but greater than about 1 hour, less than about 14 hours but greater than about 1 hour, less than about 13 hours but greater than about 1 hour, less than about 12 hours but greater than about 1 hour, less than about 11 hours but greater than about 1 hour, less than about 10 hours but greater than about 1 hour, less than about 9 hours but greater than about 1 hour, less than about 8 hours but greater than about 1 hour, less than about 7 hours but greater than about 1 hour, less than about 6 hours but greater than about 1 hour, less than about 5 hours but greater than about 1 hour, less than about 4 hours but greater than about 1 hour, less than about 3 hours but greater than about 1 hour, and less than about 2 hours but greater than about 1 hour.

In some embodiments, the cross-linked polymer matrix is degraded by heating the cross-linked polymer matrix with an acid for a time selected from the group consisting of 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, and about 48 hours.

In some embodiments, the cross-linked polymer matrix is degraded by heating the cross-linked polymer matrix with an acid for a time selected from the group consisting of less than about 48 hours but greater than about 1 hour, less than about 47 hours but greater than about 2 hours, less than about 46 hours but greater than about 3 hours, less than about 45 hours but greater than about 4 hours, less than about 44 hours but greater than about 5 hours, less than about 43 hours but greater than about 6 hours, less than about 42 hours but greater than about 7 hours, less than about 41 hours but greater than about 8 hours, less than about 40 hours but greater than about 9 hours, less than about 39 hours but greater than about 10 hours, less than about 38 hours but greater than about 11 hours, less than about 37 hours but greater than about 12 hours, less than about 36 hours but greater than about 13 hours, less than about 35 hours but greater than about 14 hours, less than about 34 hours but greater than about 15 hours, less than about 33 hours but greater than about 16 hours, less than about 32 hours but greater than about 17 hours, less than about 31 hours but greater than about 18 hours, less than about 30 hours but greater than about 19 hours, less than about 29 hours but greater than about 20 hours, less than about 28 hours but greater than about 21 hours, less than about 27 hours but greater than about 22 hours, less than about 26 hours but greater than about 23 hours, and less than about 25 hours but greater than about 24 hours.

In some embodiments, the method for recycling a cross-linked polymer matrix includes the step of recovering a degradation product of the cross-linked polymer matrix via a filtration process and/or a precipitation process.

In general, the diamino compounds of Formula (1) can be used as monomers and/or cross-linkers to make polymeric materials such as nylons, epoxies, polyurethanes, acrylamides or other type polymers or cross-linked polymers and/or materials. The diamino compounds of Formula (1) can also be used as monomers or cross-linkers for the preparation of designer materials that can further be imbued with the ability to degrade under acidic conditions. Polymer degradation can be accomplished with these materials because, inter alia, the incorporated acetal and ketal linkages are susceptible to cleavage by various chemical means. For example, the acetal and ketal linkages can be cleaved by hydrolysis under acidic conditions. Thus, use of the present diaminoacetals and diaminoketals of Formula (1) as monomers produce polymeric structure that can be predictably degraded into smaller molecular fragments under acidic conditions.

Similarly, use of the present diaminoacetals and diaminoketals of Formula (1) as cross-linkers produce polymeric materials that can be cleaved into smaller molecular fragments by cleaving the aminoacetal and aminoketals of the cross-links, for example, under acidic conditions. The rate of acid hydrolysis of acetal and ketals linkages can be used to fine-tune the physical properties of the polymeric materials. In general, the rate of acid hydrolysis decreases in the order of ketal>acetal>formal. Thus, polymeric materials that contain these acid-labile linkages can be useful in designing more environmentally sustainable materials that can degraded at will via chemical means.

In some embodiments, the epoxy resin composition disclosed herein can be used as an adhesive composition. In some embodiments, the epoxy composition disclosed herein can be used as a coating composition. In some embodiments, the epoxy composition disclosed herein can be used as an encapsulation material.

Conventional diamine compounds that feed the plastics industry are produced at high volume—often at the thousands of tons per annum scale. In order for diaminoacetals to find use in cost driven industries like the plastic industry, an economical strategy for their synthesis is a prerequisite. The present invention discloses such a strategy as the starting materials and/or precursors used in the present invention can be derived from inexpensive and readily available feedstocks. Furthermore, in the present invention, a process capable of converting the precursors into the diamino products is disclosed, and should have a high potential for translation into an optimized industrial process. Given various shortcomings of the known processes for making diaminoacetals in the prior art, the present disclosure encompassed herein now provides a strategy for the preparation of diaminoacetals with advantageous results over the methods previously known in the art. The over-all process of this invention includes two steps. In the first step, dicyanoacetals are directly prepared by the reaction of a compound containing both an alcohol group and a cyano group (now, herein referred to a cyanohydrin) with an aldehyde or ketone, (or an aldehyde or ketone equivalent). In the second step the dicyanoacetal is hydrogenated to give the corresponding diaminoacetal. A strategy which employs cyanohydrins as starting materials, as disclosed in this invention, for the production of diaminoacetals is particularly attractive because cyanohydrins can generally derived from their reaction of hydrogen cyanide (or its salts) with aldehydes, ketones, or ethylene oxide, all of with are high-volume industrial chemicals. The preparation of a dicyanoacetal and the subsequent reduction to the corresponding diaminoacetal has not been documented in the prior art.

II. EXAMPLES

Step I: Preparation of a Dicyanoacetal of Type Formula (2)

In an embodiment, the first step in the synthesis of Formula (1) is the preparation of Formula (2). Compounds of the type Formula (2) may result from the condensation of 2 molar equivalents of a cyanohydrin, with 1 molar equivalent of an aldehyde and/or ketone or an aldehyde- and/or ketone equivalent. Certain compounds of Formula (2) can be prepared from the reaction of a cyanohydrin with a ketone or ketone equivalent (a ketone equivalent is sometimes referred to as a "masked ketone"). Certain compounds of Formula (2) can be prepared from the reaction of a cyanohydrin with an aldehyde or aldehyde equivalent (an aldehyde equivalent is sometimes referred to as a "masked aldehyde"). It is know in the art that the formation of an acetal from an aldehyde/ketone and an alcohol is an equilibrium process and the position of the equilibrium is influenced by both the choice of starting alcohol and the aldehyde/ketone used. It is also known in the art that removal of water—in the case of aldehyde/ketone starting materials—or methanol (or other alcohol)—in the cased of a masked aldehyde/or ketone such as dimethoxypropane—will serve to increase the yield of acetal product. It is also known in the art that an acid can be used to catalyze the formation of acetals. However, many of the dicyanoacetals represented by Formula (2) have hitherto not been subject to synthesis in the art, and therefore represent novel compounds.

In some embodiments, the reactions to obtain polycyano compound of Formula (2) compounds, the exact molar ratio of cyanohydrin to aldehyde/ketone used can vary, but one of ordinary skill in the art can select the ratio that balances the yield of the polycyano compound of Formula (2) versus parameters such as the starting materials costs and the ability to recycle any excess starting materials or reagents. In general, it is preferable to use a molar ratio of cyanohydrin to aldehyde/ketone in a ratio of from about 4:1 to 1:1, respectively. In some embodiments, it is preferable to use a molar ratio of cyanohydrin to aldehyde/ketone of about 1:1 respectively. In some embodiments, it is most preferable to use a molar ratio of cyanohydrin to aldehyde/ketone of from about 2:4 to about 2:1, respectively. In some embodiments, it is most preferable to use a molar ratio of cyanohydrin to aldehyde/ketone of from about 2:1 to about 1;1, respectively. Specific, but non-limiting, examples of cyanohydrins are ethylene cyanohydrin (Sigma-Aldrich, Saint Louis, Mo., USA), glycolonitrile (see Organic Syntheses, Coll. Vol. 3, p. 436 (1955); Vol. 27, p. 41 (1947).), lactonitrile (Sigma-Aldrich, Saint Louis, Mo., USA), and mandelonitrile (see Organic Syntheses, Coll. Vol. 1, p. 336 (1941); Vol. 6, p. 58 (1926).). Specific, but non-limiting, examples of ketones and aldehydes are acetone, methyl ethyl ketone, cyclohexanone, cyclopentanone, acetaldehyde, benzaldehyde, butyraldehyde, formaldehyde, and isobutyraldehyde. Specific, but non-limiting, examples of ketone- and aldehyde equivalents are 2,2-dimethoxypropane, acetaldehyde dimethyl acetal, paraformaldehyde, and trioxane. In general, the condensation of a cyanohydrin with an aldehyde/ketone according to the present invention may be facilitated by the use of an acidic catalyst.

A great deal of flexibility exists with respect to the type of acid catalyst that can be used to prepare the dicyanoacetals and dicyanoaketals. The acid catalyst may be organic, inorganic, homogenous, heterogeneous or on a solid-support. Specific, but non-limiting, examples of acid catalyst that are suitable for the preparation of certain dicyanoacetals of type Formula (2) are acetic acid, Amberlyst® resins, acidic zeolites, HCl, $H_2SO_4$, p-toluenesulfonic acid, or other acid. In general, the yield of dicyanoacetals is greatly facilitated by the removal of formed water from the reaction mixture. This can be accomplished, for example, via azeotropic distillation with a Dean Stark apparatus, or with the use of an auxiliary dehydration reagent. Some specific, but non-limiting, examples of dehydration agents include, calcium chloride, calcium sulfate, magnesium sulfate, molecular sieves, and sodium sulfate. In general, when compared to distillation methods, the removal of water via the use of an auxiliary dehydration agent would add increased reagent expense to the production of a Formula (2) compound; however, many dehydration reagents can be regenerated and reused. The use of a dehydration agent may have certain advantages over distillation methods, as it can allow the preparation of Formula (2) compounds at room temperature or below, which may be advantageous with certain combinations of cyanohydrins and aldehyde/ketones. In the case of masked aldehydes/ketones such as acetaldehyde dimethylacetal or dimethoxypropane, methanol, as opposed to water, is formed during the course of dicyanoacetal formation. In such cases, it is generally advantageous to remove the formed methanol, for example, via azeotropic distillation, with a Dean-Stark apparatus or with an auxiliary material that can absorb methanol such as molecular sieves. Overall, for the formation of polycyanoacetals represented by Formula (2), a great deal of flexibility exists with regard to acid catalysts, water (or alcohol) removal conditions, temperature, and ratio of reagents/starting materials; for a given polycyano compound of Formula (2), optimal synthetic conditions can be easily determined by routing experimentation by one skilled in the art.

Step II: Hydrogenation of a Dicyanoacetal/Ketal to a Diaminoacetal/Ketal

The chemical synthesis of the polyamino acetal/ketal in accordance with the present invention can be generically represented by the synthetic scheme of FIG. 2 below.

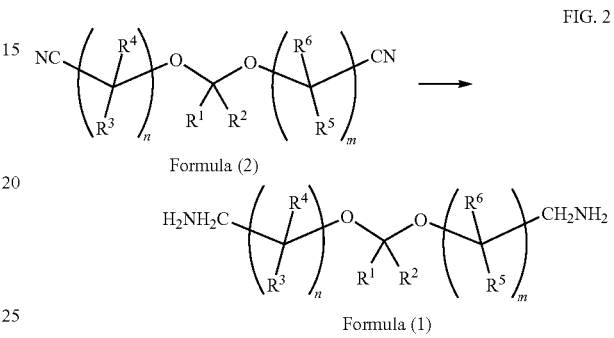

FIG. 2

In an embodiment, the transformation is carried out via a catalytic hydrogenation reaction. In an embodiment, the conversion of Formula (2) to Formula (1) may be effected in the liquid or vapor phase employing a suitable active hydrogenation catalyst. In an embodiment, conventional hydrogenation catalysts that are known in the art to effect the conversion of nitrile moieties into amines can be used. Specific, but non-limiting, examples of which may include as the active component a noble metal from the group Ru, Rh, Pd, and Pt, or a transition metal the group Cu, Cr, Co, Ni, Fe, including, but not limited to, Raney® type catalysts, Sponge Metal® type catalysts and chromite catalyst. In an embodiment, bimetallic catalysts of one or more transition metals and/or noble metals may also be used. In an embodiment the catalyst may be on a solid support. One skilled in the art, when viewing the present disclosure, will understand how to select a catalyst, including considerations of the useful life of any particular catalyst and cost. In an embodiment, an example of a preferred catalyst is a Raney® Ni or a Sponge® Ni. In an embodiment, the hydrogenation can be conducted in the liquid or vapor phase at temperatures ranging between 10° C. and 200° C. and at hydrogen pressures of 70 psi to about 5000 psi, and in another embodiment, in the temperate range between 20° C. and 150° C. and under pressures between 100 psi to about 2000 psi. In an embodiment, the conversion of Formula (2) to Formula (1) may be enhanced by the presence of ammonia during the reaction, preferably in the range, from 1 mole to 60 moles of ammonia per mole of Formula (2) used. In an embodiment, hydrogenation of Formula (2) may be carried out using anhydrous ammonia. In an embodiment, hydrogenation is carried out in aqueous ammonia. In an embodiment, an optional cosolvent(s) may be used such as, but not limited to, for example, methanol, ethanol, dioxane, and tetrahydrofuran or any solvent that is not substantially hydrogenated during the reaction or decomposed by the added ammonia. Upon the completion of the reaction, the catalyst can be removed via filtration and Formula (1) can be obtained after removal of any solvents. In an embodiment, the catalyst can be recycled. In an embodiment, the conversion of dicyanoacetals to diaminoacetals can be carried out via a batch process, using a type of batch reactor. In an embodiment, the conversion of dicyanoacetals to diaminoacetals can be carried out via continuous process, for example, by using a type of continuous reactor. In an embodiment, any excess reagent and/or solvents can be recycled. In an embodiment, Formula (2) can be further purified via distillation under reduced pressure.

The examples set forth below are intended to be illustrative and not to be construed as limiting in scope of the invention disclosed herein in any way.

Example 1: Preparation of Dicyano Acetal C-1

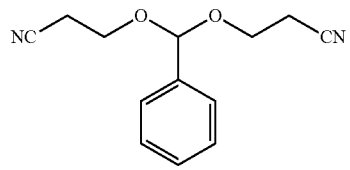 [SMILES: N#CCCOC(OCCC#N)c1ccccc1]

To a 1 L glass bottle was charged ethylene cyanohydrin (78 g), benzaldehyde (29 g), 300 mL of dichloromethane, concentrated HCl (1.1 g) and calcium sulfate (300 g). The mixture was allowed to stand at room temperature overnight, and then filtered to remove the solids. The filtrate was washed with 300 mL of a 5% NaOH solution, and 300 mL of water, and then solvent removed via rotary evaporation. The resulting crude material was further purified by heating (50-100° C.) under high vacuum (0.7 mmHg) for 2 hours, to give 37 g of dicyano acetal C-1.

Example 2: Preparation of Dicyano Acetal C-2

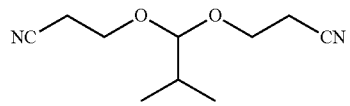

To a 10 L glass reactor equipped with internal cooling coils was charged ethylene cyanohydrin (711 g), 1 L of dichloromethane, and 3 A Molecular Sieves (600 g). The reactor was cooled to 4° C. and then isobutyraldehyde (280 g) was added in one portion. Then Amberlyst®-15 (36 g) was added in one portion, and the cooling maintained at 4-5° C. After 22 hr, an additional portion of isobutyraldehyde (50 g) was added to the reaction, and the reaction allowed to continue over night. In the following day, the reactor contents where filtered and the resultant liquid layer was washed with a 2% aqueous NaOH solution (2×5 L) and then concentrated on a rotary evaporator. The resulting crude oil crystallized upon standing, after which time the supernatant was decanted, leaving behind 470 g of dicyano acetal C-2 as crystals: $^1$H NMR (CDCl$_3$, 300 MHz): 0.95 (d, 6H), 1.92 (m, 1H), 2.62 (t, 4H), 3.68-3.76 (m, 2H), 3.79-3.86 (m, 2H), 4.23 (d, 1H).

Example 3: Preparation of Dicyano Ketal C-3

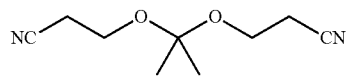

A solution comprised of ethylene cyanohydrin (426.5 g), dimethoxypropane (260.4 g), acetic acid (10 g) and methyl tert-butyl ether (1 L), was circulated through a stainless steel column (2" diameter; 5' tall) packed with 5 A molecular sieves (2 Kg). After 2 hrs of circulation, the column was drained and further washed with an additional 0.5 L methyl tert-butyl ether. The combined contents were concentrated via rotary evaporation. The resulting oil crystallized upon standing in a cold bath, and residual liquid impurities discarded. 410 g of dicyano ketal C-3 was obtained as crystals: $^1$H NMR (CDCl$_3$, 400 MHz): 1.41 (s, 6H), 2.59 (t, 4H), 2.72 (t, 4H).

Example 4: Preparation of Dicyano Acetal C-4

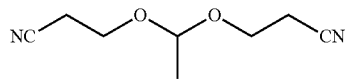

To a 1 L jacketed glass reactor was charged ethylene cyanohydrin (150 g), 1 L of dichloromethane, and 3 A Molecular Sieves (300 g). The reactor was cooled to 3° C. and then Amberlyst®-15 (10 g) was added in one portion. Acetaldehyde (90 g) was then added portion wise over a 20 min period, and the reaction allowed to progress overnight while cooling was maintained at 3-5° C. The solids where filtered off in the subsequent day, and triethylamine (5 g) was added to the liquid filtrate. The organic layer was washed with water, concentrated on a rotary evaporator, and the resultant crude oil further purified via flash distillation to yield 120 g of dicyano acetal C-4 as an oil: $^1$H NMR (CDCl$_3$, 400 MHz): 1.36 (d, J=5.2 Hz, 3H), 2.62 (t, J=6 Hz, 4H), 3.69-3.74 (m, 2H), 3.80-3.85 (m, 2H), 4.86 (q, J=5.2 Hz, 1H).

Example 5a: Preparation of Dicyano Acetal C-5

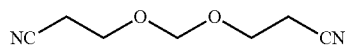 [SMILES: N#CCCOCOCCC#N]

To a 1 L three-neck Round Bottom Flask equipped with a mechanical stirrer and a Dean Stark apparatus was charged ethylene cyanohydrin (142 g), paraformaldehyde (30 g), p-toluenesulfonic acid (3 g) and 300 mL of cyclohexane. The mixture was then heated to reflux with vigorous stirring. After 2.5 hours, 19 mL of water evolved in the Dean-Stark trap, and the heating was stopped. The organic layer was washed with aqueous NaOH, water, and brine, and then concentrated on a rotary evaporator to yield the crude oil. Dicyano acetal C-5 was obtained after purification via fractional vacuum distillation.

Example 5b: Preparation of Dicyano Acetal C-5

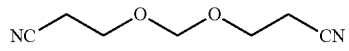 [SMILES: N#CCCOCOCCC#N]

To a 10 L glass reactor was charged ethylene cyanohydrin (426 g), paraformaldehyde (90 g), dichloromethane (1.2 L), and magnesium sulfate (21 g). The reactor was cooled to an internal temperature of −10° C. and then sulfuric acid (28 g) was added drop-wise via an addition funnel over a 1 hr period, with mechanical stirring. The reaction was continued for 1 hr, and then the contents decanted from the sludge, washed with 3% bicarbonate solution, separated, and the organic layer concentrated to give 245 g of dicyano acetal C-5 as an oil.

Example 6: Preparation of Dicyano Acetal C-6

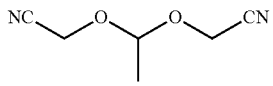

In a 500 mL jacketed reactor, was charged glycolonitrile (20 g), dichloromethane (150 mL), magnesium sulfate (21 g), and acetaldehyde (8 g). The reactor was cooled until the internal temperature reached −14° C. Then, sulfuric acid (28 g) was added drop-wise over a 5 min period, while the reaction contents were agitated with a mechanical stirrer. The addition of sulfuric acid caused a rise in internal temperature to 2° C. Once internal temperature reached −10° C., external cooling was stopped, and the reaction contents decanted. The resultant organic layer was washed with a saturated bicarbonate solution, water, and brine. The organic layer was dried over potassium carbonate and then concentrated on a rotary evaporator to give dicyano acetal C-6 as an oil: $^1$H NMR (CDCl$_3$, 400 MHz) 1.47 (d, 3H), 4.29 (d, J=16 Hz, 1H), 4.35 (d, J=16 Hz, 1H), 5.04 (q, 1H).

Example 7: Preparation of Dicyano Acetal C-7

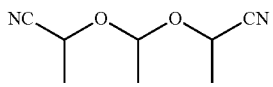

In a 500 mL jacketed reactor, was charged lactonitrile (50 g), dichloromethane (300 mL), magnesium sulfate (42 g), and acetaldehyde (16 g). The reactor was cooled until the internal temperature reached −14° C. Then, sulfuric acid (28 g) was added drop-wise over a ~1 hr period, while the reaction contents were agitated with a mechanical stirrer. After the addition of sulfuric acid was complete, the reaction was stirred for an additional 30 minutes, and then the reactor contents decanted. The resultant organic layer was washed with a saturated bicarbonate solution, water, and brine. The organic layer was dried over potassium carbonate and then concentrated on a rotary evaporator to give 30 g of dicyano acetal C-7 as an oil.

Example 8: Preparation of Diamino Acetal C-8

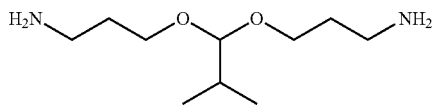

To a high pressure stainless steel reactor was charged dicyano acetal C-2 of example 2 (140 g), 700 mL of tetrahydrofuran, 700 mL of aqueous NH$_3$, and 30 g of Raney® Ni (type 2400). The reactor was then charged with hydrogen to 650 psi and the reactor contents were stirred vigorously at room temperature. The reaction progress was monitored by the pressure drop. After the reaction was judged to be complete, the catalyst was removed by filtering the reactor contents through a pad of Celite®. The filtrate was concentrated on a rotary evaporator and the crude product purified via fractional distillation under reduced pressure (1.3 mmHg) to give 110 g of diamino acetal C-8 as an oil: $^1$H NMR (CDCl$_3$, 300 MHz) 0.90 (d, J=6.9 Hz, 6H), 1.71 (pentet, 4H), 1.82-1.93 (m, 1H), 2.80 (t, 4H), 3.45-3.52 (m, 2H), 3.64-3.71 (m, 2H), 4.07 (d, J=6.6 Hz, 1H).

Example 9: Preparation of Diamino Acetal C-9

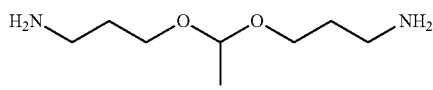

To a high pressure stainless steel reactor was charged dicyano acetal C-4 of example 4 (120 g), 600 mL of methanol, 600 mL of aqueous NH$_3$, and 24 g of Raney® Ni (type 2400). The reactor was then charged with hydrogen to 1000 psi. The reactor contents were stirred vigorously at room temperature, and then the reaction progress was monitored by the pressure drop. After the reaction was judged to be complete, the catalyst was removed by filtering the reactor contents through a pad of Celite®. The filtrate was concentrated on a rotary evaporator and the crude product purified via flash vacuum distillation to give 75 g of diamino acetal C-9. Further purification of the product was realized via fractional distillation under reduced pressure (bp=87° C.; 0.3 mmHg) to give an oil with low color.

Example 10: Preparation of Dicyano Ketal C-10

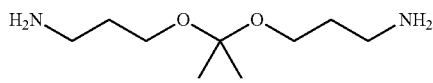

To a high pressure stainless steel reactor was charged dicyano ketal C-3 of example 3 (170 g), 540 g of methanol, 500 g of aqueous NH$_3$, and 30 g of Raney® Ni (type 2400). The reactor was then charged with hydrogen to 1000 psi. The reactor contents were stirred vigorously at room temperature and reaction progress was monitored by the pressure drop. After the reaction was judged to be complete, the catalyst was removed by filtering the reactor contents through a pad of Celite®. The filtrate was concentrated on a rotary evaporator and the crude product first purified via flash vacuum distillation, and then further purified via fractional distillation under reduced pressure to give 145 g of diamino ketal C-10 (bp=87° C.; 0.3 mmHg) as an oil with low color: $^1$H NMR (CDCl$_3$, 400 MHz) 1.33 (s, 6H), 1.41 (bs, 4H), 1.68 (pentet, 4H), 2.78 (t, 4H), 3.47 (t, 4H).

Example 11: Preparation of Diamino Acetal C-11

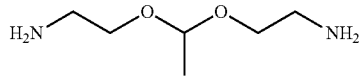

To a high pressure stainless steel reactor was charged dicyano acetal C-6 of example 6 (5.7 g), 100 ml of methanol, 100 ml of aqueous NH$_3$, and 10 g of Raney® Ni (type 2400). The reactor was then charged with hydrogen to 1000 psi. The reactor contents were stirred vigorously at room temperature. After the reaction was judged to be complete, the catalyst was removed by filtering the reactor contents through a pad of Celite®. The filtrate was concentrated on a rotary evaporator and the crude product purified via flash vacuum distillation to give the title diaminoacetal (2.5 g) as an oil: $^1$H NMR (CDCl$_3$, 300 MHz) 1.32 (d, J=5.4 Hz, 3H), 1.48 (bs, 4H), 2.86 (t, 4H), 3.42-3.48 (m, 2H), 3.59-3.66 (m, 2H), 4.73 (q, 1H).

Example 12: Preparation of Diamino Acetal C-12

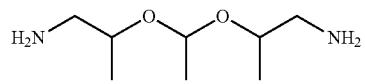

To a high pressure stainless steel reactor was charged dicyanocetal C-7 of example 7 (2.7 g), 50 ml of methanol, 50 ml of aqueous NH$_3$, and 3 g of Raney® Ni (type 2400). The reactor was then charged with hydrogen to 1000 psi. The reactor contents were stirred vigorously at room temperature. After the reaction was judged to be complete, the catalyst was removed via filtration. The filtrate was concentrated on a rotary evaporator and the crude product purified via flash vacuum distillation to give diamino acetal C-12 (1 g) as an oil: obtained as a mixture of diastereomers; $^1$H NMR (CDCl$_3$, 300 MHz) 1.11 (d, J=6.3 Hz), 1.17 (d, J=6.3 Jz), 1.18 (d, J=6.3 Hz), 1.32 (d, J=5.1 Hz), 1.33 (d, J=5.1 Hz), 1.41 (bs, 4H), 2.62-2.74 (m, 4H), 3.55-3.75 (m, 2H), 4.75-4.79 (m, 1H).

Example 13: Preparation of Diamino Acetal C-13

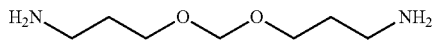

To a high pressure stainless steel reactor was charged dicyanoacetal C-5 of example 5 (9 g), 200 mL of methanol, 200 mL of aqueous NH$_3$, and 10 g of Raney® Ni (type 2400). The reactor was then charged with hydrogen to 1000 psi and the reactor contents were stirred vigorously at room temperature. After the reaction was judged to be complete, the catalyst was removed by filtration. The filtrate was concentrated on a rotary evaporator and the crude product purified via flash vacuum distillation under reduced pressure to give 7 g (bp=80-90 @ 0.3 mmHg) of the title diaminoacetal as an oil: $^1$H NMR (CDCl$_3$, 400 MHz) 1.32 (bs, 4H), 1.72 (pentet, 4H), 2.80 (t, J=6.8 Hz, 4H), 3.60 (t, J$_{av}$=6.2 Hz, 4H), 4.62 (s, 2H).

Example 14: Preparation of Diamino Acetal C-14

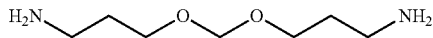

To a high pressure stainless steel reactor was charged dicyanoacetal C-5 of example 5 (20 g), 200 mL of methanol, 200 mL of aqueous NH$_3$, and 10 g of Sponge Nickel (type A-4000). The reactor was then charged with hydrogen to 1000 psi and the reactor contents were stirred vigorously at room temperature. After the reaction was judged to be complete, the catalyst was removed by filtration. The filtrate was concentrated on a rotary evaporator and the crude product further purified via flash distillation under reduced pressure to give title diamino acetal C-14 as an oil. The compound was further purified via fractional vacuum distillation (bp=73-74 @ 0.17 mmHg).

Example 15

The addition of conventionally used polyamine hardeners in the art of epoxy has been found to have a deleterious effect on the recycling, removal, or dissolving the epoxy compositions according to the present invention. The incorporation of only 2% chemical equivalents of the conventionally used "non-degradable" polyamines can begin to inhibit the full dissolution of the epoxy compositions, and about 20% chemical equivalents is about enough to prevent the matrix from dissolving under the acidic conditions detailed in the is invention. For example, a cured epoxy composition consisting of a bisphenol A-type epoxy resin (EEW=188) and a compound type of formula (1) diamine (AEW=40.5), and the diamine under the trade name EDR-148 (AEW=37) gave the following results the following Table 1:

TABLE 1

| Parts Resin | Parts Cleavable Hardener | Parts EDR-148 | equivalence of DER-148 | Wt % dissolved Epoxy |
|---|---|---|---|---|
| 200 | 44 | 0 | 0% | >99% |
| 200 | 43 | 1 | 2.5% | >95% |
| 200 | 42 | 2 | 5% | ~30% |
| 200 | 40 | 4 | 10% | ~15% |
| 200 | 36 | 8 | 20% | None |

However, when conventionally used polyamine hardeners are combined with the acid-labile polyamine curing agent of Formula (1), properties of epoxy resin compositions, containing both acid degradable and non-degradable cross-links, can be tuned on the basis of the relative proportions of the polyamines used.

III. ALTERNATIVE PROCESSES

In one embodiment, the present invention provides a process chemical synthesis for the preparation of di-(2-aminoethyl) formal acetal of formula I. In one embodiment, the process comprises reacting a compound of formula Va with a second compound selected from the group consisting of ammonia, ammonium salt, and combinations or equivalents (such as ammonium hydroxide) thereof, to form di-(2-aminoethyl) formal acetal of formula I:

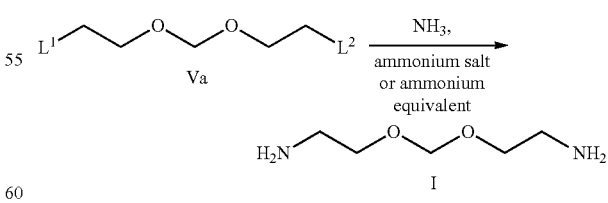

wherein L$^1$ and L$^2$ are the same or different and each is independently a leaving group or leaving group precursor. In one embodiment, each of L$^1$ and L$^2$ is independently selected from the group consisting halogen or an alkyl- or aryl-sulfonyloxy group. In one embodiment, each of L$^1$ and L$^2$ is independently selected from the group consisting of a chloro, a bromo, an iodo, a mesyloxy, a besyloxy and a tosyloxy group. In one embodiment, each of $L^1$ and $L^2$ is independently selected from the group consisting of a halide, methanesulfonate, para-toluenesulfonate, trifluoromethane sulfonate, mono nitro and dinitro phenolate.

In some embodiments, the process chemical synthesis for the preparation of di-(2-aminoethyl) formal acetal of formula I further comprises adding an additive to the reaction. In one embodiment, the additive is an iodide salt. In one embodiment, the iodide salt is a potassium iodide or a sodium iodide or a combination of both.

In some embodiments, the process chemical synthesis for the preparation of di-(2-aminoethyl) formal acetal of formula I, the reaction is conducted at a temperature range of from about 0° C. to 200° C. In one embodiment, the reaction is conducted at a temperature range of from about 40° C. to 140° C. In one embodiment, the reaction is optionally conducted in the presence of a solvent. In one embodiment, the solvent is selected from the group consisting of water, methanol, ethanol, dioxane and combinations thereof.

In some embodiments, the process chemical synthesis for the preparation of di-(2-aminoethyl) formal acetal of formula I, the reaction is conducted in a pressurized system. In one embodiment, the reaction is conducted in the presence of excess ammonia or ammonia equivalents. In one embodiment, the molar proportion of the ammonia or ammonia equivalents to the compound of formula Va is about 20:1. In one embodiment, the molar proportion of the ammonia or said ammonia equivalents to the compound of formula Va is greater than about 20:1. In one embodiment, the molar proportion of the ammonia or the ammonia equivalents to the compound of formula Va is less than about 20:1.

In some embodiments, the process of chemical synthesis for the preparation of di-(2-aminoethyl) formal acetal of formula I comprises reducing di-(2-nitroethyl) formal acetal Vb with a reducing agent to form the compound formula I:

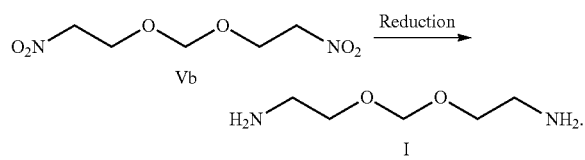

In one embodiment, the reducing agent is hydrogen gas in the presence of a catalyst. In one embodiment, the reducing agent is selected from the group consisting of hydrogen in the presence of catalytic Raney nickel, hydrogen in the presence of catalytic Palladium on carbon (Pd/C), catalytic Pd/C and ammonium formate in methanol, hydrogen in the presence of catalytic $PtO_2$, iron metal in the presence of acid, and iron metal/$FeCl_3$ in the presence of acid. In one embodiment, the hydrogenation catalyst is recovered and recycled. In one embodiment, the hydrogenation catalyst is recovered via filtration after the reaction is complete. In one embodiment, the reaction is conducted at a temperature range of from about 20° C. to 200° C. In one embodiment, the reaction is conducted at a temperature range of from about 40° C. to 140° C. In one embodiment, the reaction is conducted under hydrogen gas pressure of from about 1 atm to about 1000 atm.

In some embodiments, the process of chemical synthesis for the preparation of di-(2-aminoethyl) formal acetal of formula I comprises reacting ethanolamine with paraformaldehyde or any suitably masked formaldehyde equivalent in the presence of an acid to form di-(2-aminoethyl) formal acetal salt of formula VIII; and reacting said di-(2-aminoethyl) formal acetal salt VII with a base to form di-(2-aminoethyl) formal acetal I:

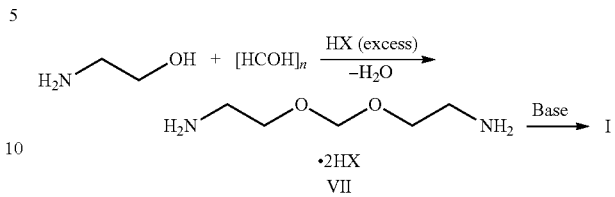

In one embodiment, the acid is an inorganic acid. In one embodiment, the acid is selected from the group consisting of HCl, HBr and $H_2SO_4$. In one embodiment, the acid is an organic acid. In one embodiment, the organic acid is p-toluenesulfonic acid, acetic acid or methanesulfonic acid. In one embodiment, the suitably masked formaldehyde equivalent is trioxane. In one embodiment, the ratio of a molar equivalence of the acid to ethanolamine is greater than 1. In one embodiment, the ethanolamine is pretreated with an acid prior to the reaction with the paraformaldehyde or the any suitably masked formaldehyde equivalent. In one embodiment, the process further comprises the step of adding a drying agent to the reaction mixture. In one embodiment, the drying agent is anhydrous magnesium sulfate ($MgSO_4$). In one embodiment, the drying agent is anhydrous sodium sulfate ($Na_2SO_4$) or anhydrous potassium sulfate ($K_2SO_4$). In one embodiment, the process is conducted under Dean-Stark type reaction condition to remove any water formed during the reaction. In one embodiment, the process is conducted at temperature ranging from about 0° C. to about 220° C.

In some embodiments, the process of chemical synthesis for the preparation of di-(2-aminoethyl) formal acetal of formula I comprises reacting ethanolamine with a formylacetal of formula VIII to form di-(2-aminoethyl) formal acetal salt of formula VII; and reacting the di-(2-aminoethyl) formal VIII alt of formula VII with a base VII di-(2-aminoethyl) formal acetal of formula I:

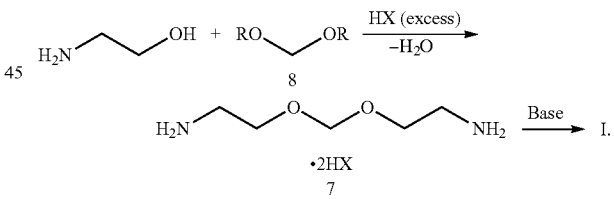

In some embodiments, the present invention provides a process of chemical synthesis for the preparation of di-(3-aminopropyl) formal acetal of formula X. In one embodiment, the process comprises a catalytic hydrogenation reaction of a compound of formula IX:

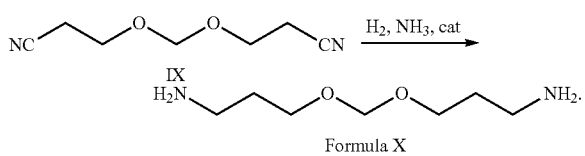

Epoxies are an important class of thermosetting polymers. Epoxy resins are typically hardened or cured by a cross-linking reaction using one of three general methods. The chemistry of epoxy curing is explained in great detail in the Handbook of Composites (edited by S. T. Peters, Chapter 3, pp 48-74, published by Chapman & Hall, 1998). The properties and applications of cured resin are greatly influenced by the choice of the hardener formulation or the method of curing.

One method is simply the reaction of the epoxy resin with itself (i.e. homopolymerization) via a ring-opening polymerization mechanism of the epoxy groups. The self-curing of epoxy resins usually requires an elevated temperature but can be initiated with either a Lewis acid- or a Lewis base catalyst (as opposed to a curing agent).

In the second method, the epoxy resin is cured with a cyclic acid anhydride. The anhydride can react with the epoxy group, pendant hydroxyls, or residual water to form a carboxylate intermediate, which then reacts with the epoxy group, causing a self-perpetuating reaction between the anhydride and the epoxy resin. Catalytic amounts of tertiary amines are commonly used as additives as they facilitate the opening of the anhydride. Typically, anhydride epoxy formulations generally do not readily cure at room temperature, and are generally cured at elevated temperatures.

In the third method, the epoxy resin reacts with polyvalent nucleophiles such as polyamines to form a polymeric network of essentially infinite molecular weight. Epoxy groups will react with potentially every amine containing an active hydrogen atom, so that a simple diamine (NH2-R—NH2) acts as a tetra-functional cross-linker, reacting with four epoxy groups. The ring opening of the epoxy ring with a primary or secondary amine generates a stable C—N bond, and the reaction is essentially irreversible. Aliphatic polyamines are widely used in ambient temperature curing compositions. Aromatic amines are generally less reactive than aliphatic amines, so they are primarily used in elevated temperature curing compositions. The use of aromatic diamine hardeners such as 4,4'-methylenedianiline (MDA) or 4,4'-diaminodiphenyl sulfone (DDS) are commonly used in epoxy applications that require enhanced temperature properties such as high glass transition temperature (Tg) or in composite manufacturing techniques that require long pot-life at ambient temperature such as a pre-impregnated ("prepreg") method, wherein, for example, composite fibers may already have a material such as an epoxy present.

Epoxies serve massive global markets in adhesives and coatings, and are also one of the industry standard thermosetting plastic matrices used for construction of fiber reinforced plastic (FRP). FRPs are composite materials consisting of a polymer matrix and a fiber such as carbon fiber, fiberglass, aramid fiber, natural fiber, or other fiber. The fiber serves to enhance the properties of the plastic in areas such as strength and elasticity. FRPs are also commonly referred to as "plastic composites" or, for simplicity, just "composites." The term "plastic composites" can also embody plastic materials that have non-fibrous entities incorporated in them such as metals or nanomaterials. Plastic composites provide lightweight alternatives to other structural materials (e.g., steel or aluminum) and are widely used in the automotive, aerospace, nautical craft, wind energy, and sporting goods sectors. The incorporation of lightweight composites can offer substantial environmental benefits by way of leading to increased energy efficiency; yet, the positive impact of thermosetting plastic composites is offset by their lack of recyclability and persistence in the environment. The predicted waste accumulation in the growing wind power industry is an illustrious example. The current output of wind energy is approximately 10 times that of the production in 1980, and windmill blade propellers can reach over 60 meters in length. The material wastage from wind motor blade production is estimated to reach 225,000 tons per year by 2034. The weight percentage of epoxy in fiber reinforced epoxies typically is in the range of 25-40%. The raw materials (i.e. the plastic and fiber) that go into composite construction can be expensive, and are usually of petrochemical origins. Thus, there are both economic and environmental drivers for the development of new reworkable epoxy thermosetting compositions that would enable the manufacture of recyclable fiber reinforced epoxy composites.

Of the three general epoxy curing methods describe above, epoxy compositions based on diepoxides ("resin") and polyamines ("hardener") to form a cross-linked polymeric network of essentially infinite molecular weight are very common (the combination of "resin+hardener" is sometimes referred to as "cured epoxy" or "cured resin" or simply "resin" or epoxy). The widespread utility of such epoxy formulations for composite manufacturing and other structural applications is due to their generally excellent processablity prior to curing and their excellent post-cure adhesion, mechanical strength, thermal profile, chemical resistance, etc. Further, the high-density, three-dimensional network of epoxies makes epoxies robust materials, tolerant of a wide range of environmental conditions. At the same time, the cross-linked network makes the removal, recycling, and/or reworkability of epoxy, or epoxy-based materials, notoriously difficult. The cross-linking reactions that occur with conventionally used polyamine epoxies formulation are essentially irreversible; therefore, the material cannot be re-melted and re-shaped without decomposition; the material cannot be readily dissolved either. As a result, fiber reinforced epoxies or epoxy-based composite materials are not amenable to standard recycling practices because the epoxy matrix and fibers cannot be readily separated, and recovered. Thermosetting composites are typically disposed of in landfills, or by burning. An emerging technology for disposal of carbon fiber composites involves special incinerators burn away the plastic matrix of the composite, leaving behind the carbon fiber, which then can be reclaimed. However, the value of the thermoset matrix is not extracted in a repurposable from as it is destroyed in the incineration process.

The intractability of a cured epoxy resin stems, primarily, from its highly cross-linked network. Those in the art can understand that if the links in the three-dimensional network can be cleaved under controlled conditions, then the network can be disassembled into smaller, soluble molecules and/or polymers, and therefore the cured matrix can potentially be separated and recovered from the fiber in a composite. By providing for the manufacture of recyclable epoxy composites, components of the plastic matrix and components of the reinforcement material can be recovered by way of a recycling step. In principal, such type of recyclable epoxy compositions can be accomplished through use of either a dissolvable (or degradable) resin or a curing agent that contains a bond capable of cleavage under a specific set of conditions. The majority of the prior art on cleavable epoxy compositions has been focused on incorporation of different cleavable groups in the resin component. Such reports are also geared toward the use of epoxy as a reworkable adhesive for electronics applications that allow glued or encapsulated components to be debonded under a specific set of conditions. Selected examples of such reworkable epoxy compositions include U.S. Pat. Nos. 5,932,682, 5,560,934, and 5,512,613, each referring to a reworkable epoxy thermosetting composition based on a diepoxide component in which the moiety connecting the two epoxy groups is an acid labile acyclic ketal or acetal linkage. The cured resins are shown to be useful for adhesives and for electronic encapsulates for use as removable electronic encapsulation. The anhydride-cured resins are shown to disassemble in acidic environments.

U.S. Pat. No. 6,887,737 B1 refers to a reworkable epoxy thermosetting composition based on a resin component that contains at least two cleavable acetal or thioacetal linkages. The described epoxy compositions are thermally reworkable.

U.S. Pat. No. 6,657,031 B1 describes thermally reworkable epoxy compositions for use in electronic underfills based on a diepoxide component that contains thermally labile ester linkages, allowing bonded electronic components to more easily be detached after heating.

As disclosed herein for the first time, a reworkable epoxy composition that is designed to have cleavable linkages in the hardener components, as opposed to the resin component, is more attractive on both performance and economic grounds. The skilled artisan will understand that hardener components of epoxy compositions are often interchanged. The skilled artisan will understand that the volume percentage of a hardener is significantly less than that of the resin component in commonly used epoxy compositions (i.e. any added cost is more diluted). The skilled artisan will understand that the industrial standard epoxy resin used for structural and composite applications is the diglycidyl ether of bisphenol A (DGEBPA) of various grades. As will be illustrated by the disclosure encompassed herein, the breaking of cross-links in reworkable epoxy compositions derived from amino curing agents with cleavable linkages and diepoxide resins can lead to the formation of linear polymers. The present disclosure thereby provides a mechanism for the transformation of a thermosetting matrix into a thermoplastic, which is a recyclable material. As disclosed herein, the molecular structure of the cleavable linkage in the hardener is paramount to the degradation ability of the thermoset matrix in the ambient environment, and just the same, the ease or difficulty of the reworkability or recycling of the cured epoxy compositions. Ideally, degradation would not occur in the materials' ambient environment, but only when recycling is selectively desirable.

International Patent Application No. PCT/CN2011/076980 discloses the use of acid liable amine hardeners for reworkable epoxy compositions. Specifically, the use of aminoacetal, aminoketal, aminoorthoester, or aminoorthocarbonate hardeners with epoxy resins is described. When immersed in acidic environments, the cross-links that make up the three-dimensional network of the cured epoxy, breakdown, and the cured-epoxy can be dissolved. The ease or difficulty of epoxy dissolution can be controlled by the type of hardener employed. International Patent Application No. PCT/CN2012/075084 discloses the use of acid liable amine hardeners for reworkable epoxy compositions containing one or more reinforcing components. When immersed in acidic environments, the cross-links that make up the three-dimensional network of the cured, reinforced epoxy break down. The cured-epoxy can be dissolved and the reinforcing components recovered. The ease or difficulty of epoxy dissolution can be controlled by the type of hardener employed.

Existing thermosetting composite recycling technology entails the incineration of the plastic constitution of the material and recovery the reinforcement fiber. In an embodiment as encompassed herein, the use of reworkable epoxy compositions to fabricate composites provides a more fully recyclable approach because it enables both plastic and fibers to be recovered from the composite. In an embodiment, the cross-linked epoxy resin degrades into epoxy-based polymers or smaller molecular fragments, which may be thermoformable and have useful properties. As will be understood by the skilled artisan, epoxy thermoplastics are engineered polymers that can be used in other industrial applications. The polymer obtained from recycling may be reused or repurposed in other applications that are well suited for thermoplastics such as powder coatings, laminates, injection molding, compression molding, etc.

In an embodiment, the combined mass recovery of the reinforcement materials and epoxy degradation material can exceed 80%, and the reinforcement material can be recovered in good form provided that it is sufficiently stable to the basic recycling conditions. In an embodiment, the recycling methods of the reworkable epoxy resin compositions and products/composite materials encompassed herein are relatively mild, economical, and easy to control. For example, the processes can be simple enough to be performed at the site of product manufacturing, whereby prost-production epoxy scrap waste could be recycled instead of being thrown in the landfill.

The economic implications of the disclosed reworkable epoxy compositions for composite product manufactures are potentially substantial, as it allows value to be extracted back from expenditures and manufacturing costs. Thus, the present disclosure meets a primary objective behind recycling—in addition to environmental protection—in that it demonstrates the breakdown of end-of-life products in to their raw material and/or high value material that can be reused to make new products. It also fulfills the long-term goals of the cradle-to-cradle life cycle in that it helps promote recycling as a prime alternative source to raw materials.

This disclosure relates, in part, to processes for the preparation of polyaminoacetals, including the compound of formula (I), also known as di-(2-aminoethyl) formal acetal:

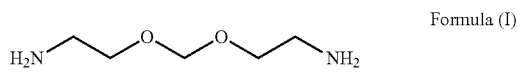

Formula (I)

In an embodiment, encompassed herein are processes for the preparation di-(2-aminoethyl) formal (Formula I).

Formula I contains an acetal group, specifically a formal group, which links two primary amine end groups. Because Formula I contains two primary amine groups, it can be used to make polymeric materials (e.g., nylons) or cross-linked polymers such as epoxies or polyurethanes, by way of several non-limiting examples. Polymeric materials derived from Formula I may be degradable under acidic conditions by way of the acetal linkage, which is acidic labile. Degradable polymeric materials may have a variety of applications. A synthetic process for the preparation of di-(2-aminoethyl) formal that is both economical and amenable to multi-ton scale synthesis could enable the cost-effective manufacture of degradable materials. Encompassed herein are multiple different synthetic routes that may be used for the preparation of di-(2-aminoethyl) formal.

In an embodiment, a direct and economical route for the preparation of Formula I is a single-step sequence involving the direct reaction of ethanolamine with formaldehyde. However, this process does not lead to the formation of I, but instead leads to the production of a 1,3,5-triazine (Formula II) as show in scheme 1.

Scheme 1

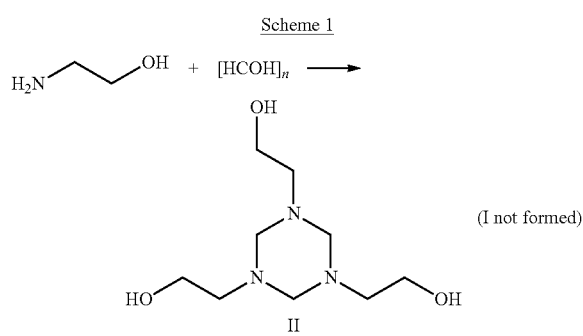

(I not formed)

The production of Formula II can easily be rationalized by the fact that the more reactive amino group of ethanolamine reacts with formaldehyde, instead of the less reactive hydroxyl group. Suitably protected ethanolamine derivatives, such as, but not limited to, N-(2-hydroxyethyl)phthalimide, can be used in place of ethanolamine to provide Formula I in a two step sequence as is shown in scheme 2. This general approach is the most used method for the preparation of Formula I in the prior art as is documented, for example, in U.S. Pat. No. 5,191,015. The reported overall yield for this sequence is generally in the range of 50-60%. While this documented procedure is relatively straightforward to perform in the laboratory setting, the process is not ideal for a multi-ton industrial process. The method is not atom economical as nearly 5 ton of the N-(2-hydroxyethyl)phthalimide (III) starting material would be required for the production of every 1 ton of Formula I.

Scheme 2

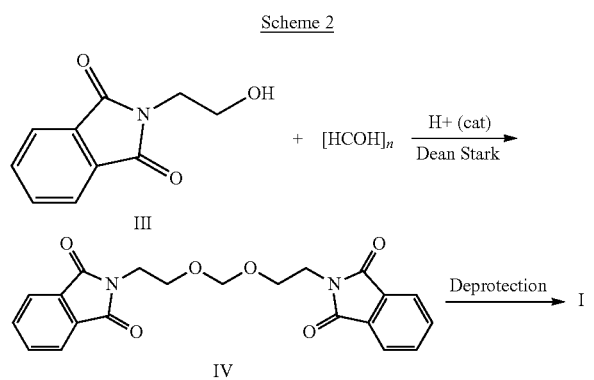

U.S. Pat. No. 2,409,675 is the other documented process for the preparation of di-(2-aminoethyl) formal of Formula I in the prior art. The patent discloses preparation of Formula I via a multi-step method that generally entails: 1) the reaction of glyconitrile with excess of an acetal; 2) hydrogenation of the resulting unsymmetrical cyanoacetal in the presence of ammonia and a hydrogenation catalyst; 3) treatment of the unsymmetrical cyanoacetal with excess of acid, which promotes a disproportiaonation reaction and leads to the salt of di-(2-aminoethyl) formal; and 4) isolation of I after deprotonation with a base. U.S. Pat. No. 2,409,675 discloses a multi-step chemical synthesis of di-(2-aminoethyl) formal acetal (I) according to the following Scheme 3:

Scheme 3

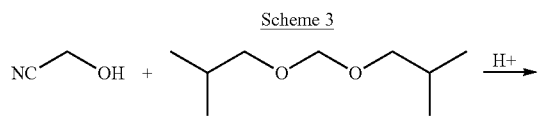

-continued

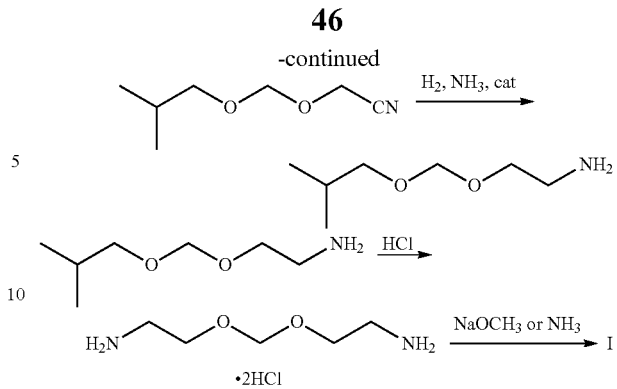

The invention is further described by the following examples. It should be recognized that variations based on the inventive features are within the skill of the ordinary artisan, and that the scope of the invention should not be limited by the examples. To properly determine the scope of the invention, an interested party should consider the claims herein, and any equivalent thereof. In addition, all citations herein are incorporated by reference, and unless otherwise expressly stated, all percentages are by weight.

In another embodiment, encompassed herein are processes for the preparation di-(3-aminopropyl) formal (Formula X).

Formula X

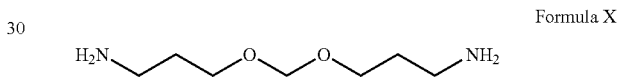

Formula X contains an acetal group, specifically a formal group, which links two primary amine end groups. Because Formula X contains two primary amine groups, it can be used to make polymeric materials (e.g., nylons) or crosslinked polymers such as epoxies or polyurethanes, by way of a few non-limiting examples. Polymeric materials derived from Formula X may be engendered with the property of degradability under acidic conditions because the said compound contains an acetal linkage, which is acidic labile. Degradable polymeric materials may have a variety of applications. A synthetic process for the preparation of di-(3-aminopropyl) formal that is both economical and amenable to multi-ton scale synthesis could enable the cost-effective manufacture of degradable materials. In an embodiment, the disclosure encompassed herein describes several different synthetic routes that may be used for the preparation of di-(3-aminopropyl) formal.

Given various shortcomings of the known processes for making di-(2-aminoethyl) formal acetal, a need exists for economical and scalable synthetic processes for the preparation of di-(2-aminoethyl) formal acetal and related compounds. As described herein, the disclosure encompassed herein now provides multiple processes for the preparation of the molecules described herein, with advantageous results over the methods previously known in the art.

In an aspect the present invention provides a set of processes of chemical synthesis that may be used for the preparation of polyaminoacetals. In an embodiment, a process of chemical synthesis of di-(2-aminoethyl) formal acetal I is described. In one embodiment, said process comprises reacting a compound of formula Va with a second compound selected from the group consisting of ammonia, ammonium salt, and combinations or equivalents (such as ammonium hydroxide) thereof, to form a compound formula I, wherein $L^1$ and $L^2$ are the same or different and each is independently a leaving group or leaving group precursor.

Scheme 4.

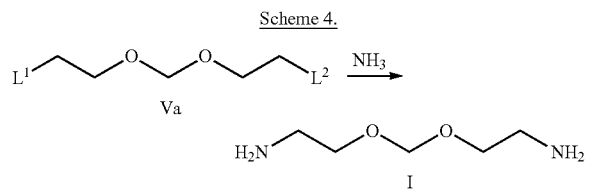

In an embodiment, each of $L^1$ and $L^2$ is independently selected from the group consisting halogen or an alkyl- or aryl-sulfonyloxy group. In an embodiment, each of $L^1$ and $L^2$ is independently selected from the group consisting of a chloro, a bromo, an iodo, a mesyloxy, a besyloxy and a tosyloxy group. In another embodiment, each of $L^1$ and $L^2$ is independently selected from the group consisting of a halide, methanesulfonate, para-toluenesulfonate, trifluoromethane sulfonate, mono nitro and dinitro phenolate.

In some embodiments, said process of chemical synthesis of di-(2-aminoethyl) formal acetal I further comprises adding an additive to the reaction. In one embodiment, said additive is an iodide salt. In a further embodiment, said iodide salt is a potassium iodide or a sodium iodide or a combination of both.

In an embodiment, the substitution reaction is conducted at a temperature range of from about 0° C. to 200° C. In an embodiment, the substitution reaction is conducted at a temperature range of from about 40° C. to 140° C. In another embodiment, the substitution reaction is optionally conducted in the presence of a solvent. In another embodiment, the substitution reaction is optionally conducted in the presence a solvent is selected from the group consisting of, but not limited to, water, methanol, ethanol, dioxane and combinations thereof. In an embodiment, the substitution reaction is conducted in a pressurized system, at a pressure selected based on the desired reaction properties and results. In an embodiment, the substitution reaction is conducted in the presence of excess ammonia or ammonia equivalents. In one embodiment, the molar proportion of ammonia or ammonia equivalent to the compound of formula (5) is about 20:1. In another embodiment, the molar proportion of ammonia or ammonia equivalent to the compound of formula Va is greater than about 20:1. In another embodiment, the molar proportion of ammonia or ammonia equivalent to the compound of formula Va is less than about 20:1.

In an embodiment, I is isolated by distillation of the reaction mixture. In another embodiment, I is isolated by extracting the reaction mixture with a solvent followed by evaporation of the solvent and/or distillation of the extract.

In some exemplary embodiments of a process of chemical synthesis of di-(2-aminoethyl) formal acetal I, the process comprises reducing di-(2-nitroethyl) formal acetal Vb with a reducing agent to form the compound formula I as shown in scheme 5 below:

Scheme 5.

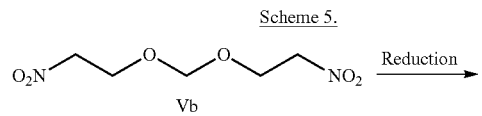

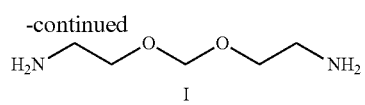

In an embodiment, the reducing agent is hydrogen gas in the presence of a catalyst. In one embodiment, reducing agent is selected from the group consisting of hydrogen in the presence of catalytic Raney nickel, hydrogen in the presence of catalytic Palladium on carbon (Pd/C), catalytic Pd/C and ammonium formate in methanol, hydrogen in the presence of catalytic $PtO_2$, iron metal in the presence of acid, and iron metal/$FeCl_3$ in the presence of acid.

In another embodiment, the hydrogenation catalyst is recovered and recycled. In another embodiment, the hydrogenation is recovered via filtration after the reaction is complete. In an embodiment, the reaction is conducted at a temperature range of from about 20° C. to 200° C. In an embodiment, the reaction is conducted at a temperature range of from about 40° C. to 140° C. As will be understood based on the disclosure set forth herein, the selected temperature may vary depending upon the catalyst used, etc. . . . . . In an embodiment, I is isolated by distillation of the reaction mixture. In another embodiment, I is isolated by extracting the reaction mixture with a solvent followed by evaporation of the solvent and/or distillation of the extract. In another embodiment, I is isolated by filtration of the reaction mixture followed by distillation of the filtrate.

In some embodiments, the reaction is conducted under hydrogen gas pressure of from about 1 atm to about 1000 atm.

In some exemplary embodiments of a process of chemical synthesis of di-(2-aminoethyl) formal acetal I, said process comprising reacting ethanolamine with paraformaldehyde or any suitably masked formaldehyde equivalent in the presence of an acid to form di-(2-aminoethyl) formal acetal salt VII; and reacting said di-(2-aminoethyl) formal acetal salt VII with a base to form di-(2-aminoethyl) formal acetal I as shown in scheme 6 below.

Scheme 6

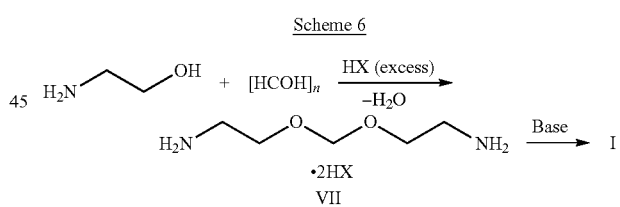

In one embodiment, said acid is an inorganic acid. In another embodiment, said acid is selected from the group consisting of HCl, HBr and $H_2SO_4$. In an embodiment, said acid is an organic acid. In another embodiment, said organic acid is p-toluenesulfonic acid, acetic acid, or methanesulfonic acid.

In one embodiment, the suitably masked formaldehyde equivalent is trioxane. In another embodiment, the ratio of the molar equivalence of the acid to ethanolamine is greater than 1. In some embodiments, ethanolamine is pretreated with an acid prior to the reaction with the paraformaldehyde or the any suitably masked formaldehyde equivalent.

In some embodiments, the process of chemical synthesis of scheme 6 further comprises an adding a drying agent to the reaction mixture. In one embodiment, said drying agent is anhydrous magnesium sulfate ($MgSO_4$). In another embodiment, said drying agent is sodium sulfate ($Na_2SO_4$)

or potassium sulfate ($K_2SO_4$). In some embodiments, the process of chemical synthesis of scheme 6 is conducted under Dean-Stark type reaction condition to remove any water formed during the reaction. In some embodiments, the process of chemical synthesis of scheme 6 is conducted at temperature ranging from about 0° C. to about 220° C.

In some exemplary embodiments, a process of chemical synthesis of the present invention comprises reacting ethanolamine with a formylacetal VIII to form di-(2-aminoethyl) formal acetal salt VII; and reacting said di-(2-aminoethyl) formal acetal salt VII with a base to form di-(2-aminoethyl) formal acetal I as shown in scheme 7 below.

Scheme 7

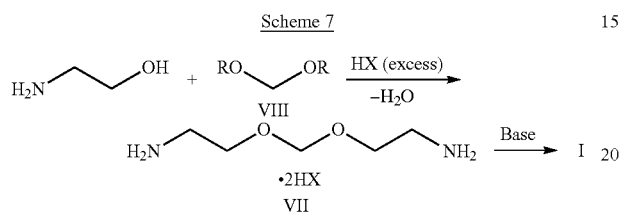

Example 1: Preparation of I Via the Ammonolysis of Di-(2-Chloroethyl) Formal (Formula V)

The key embodiment of this example is the formation of Formula I via the ammonolysis of di-(chloroethyl) formal (Formula V).

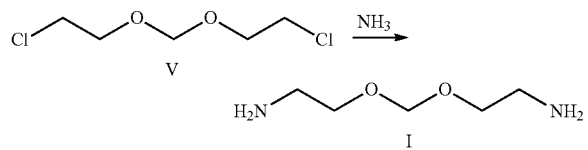

The synthesis of Formula V can be readily achieved from the reaction of 2-chloroethanol and formaldehyde (which can be employed in solid form as paraformaldehyde or trioxane), which are relatively inexpensive raw materials. There are well established processes for the preparation of Formula V, which are suitable for large scale preparation. The key reaction of this example is the alkylation reaction between 2 equivalents of ammonia and Formula V to form Formula I. In an embodiment, this reaction can be carried out according to standard reaction protocols that involve the reaction of an alkyl chloride with ammonia or ammonia equivalent like ammonium hydroxide. In an embodiment, the reaction is amenable to being carried out in a pressure vessel in a batch process, or in a continuous reactor in a continuous process. In an embodiment, Formula I can be prepared by the reaction of di-(2-chloroethyl) formal Formula V with an excess of anhydrous liquid $NH_3$ in an autoclave reactor or under pressurized conditions, such as in a pressure vessel. $NH_3$ should be used in excess to minimize the amount of multiple alkylation byproducts. In the case of a dialkyl chloride like Formula V, multiple alkylation would lead to the formation of oligomers (or even crosslinking). While the complete avoidance of such byproducts may be unavoidable in the ammonolysis of Formula V, Formula I may still be obtained in sufficient purity via distillation due to its lower vapor pressure (relative to its oligomeric counterparts). The preferred molar proportion of $NH_3$/Formula V is 20:1, but in various embodiments, this ratio can be greater than or less than 20:1. While in preferred embodiments, the reaction is carried out without a solvent, in other embodiments, the reaction may be carried out in a solvent. Non-limiting examples of optional solvents include, independently or in combination, water, methanol, ethanol, and dioxane. The reaction can be carried out in the range from 20° C. to 200° C., and in an embodiment, in the range of 40° C. to 140° C. In an embodiment, the reaction time and yield may be increased by the addition of additives, such as, but not limited to, NaI. In an embodiment, upon completion of the reaction, any excess of ammonia can be released. In an embodiment, the ammonia can be captured for recycling. Formula I can be isolated via distillation after filtration of $NH_4Cl$ or other salts. In an embodiment, molecular species having basic pH characteristics can be added to aid in purification. In another embodiment, Formula I can be purified via an extraction process and subsequent distillation.

Example 2: Preparation of Formula I Via the Reduction of Di-(2-Nitroethyl) Formal (Formula VI)

The key embodiment of this example is the formation of Formula I via the reduction of di-(2-nitroethyl) formal (Formula VI).

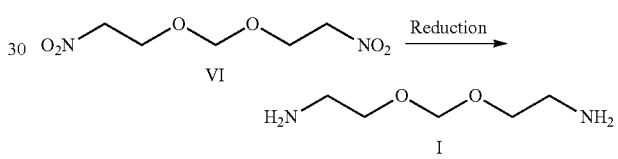

The synthesis of Formula VI can be accomplished via the reaction of 2-nitroethanol and formaldehyde (which can be employed in solid form as paraformaldehyde or trioxane) such as using the procedures detailed for dinitro acetal compounds in U.S. Pat. No. 2,415,046 or U.S. 2009/0216049 A1. There are a variety of common conditions used by those skilled in the art for the reduction of aliphatic nitro compounds to the corresponding amines. The conversion of Formula VI to Formula I may be accomplished using such protocols. By way of a non-limiting example, such protocols include catalytic hydrogenation reaction using Raney nickel, catalytic hydrogenation reaction using Palladium on carbon (Pd/C), catalytic reduction using Pd/C and ammonium formate in methanol, catalytic hydrogenation using $PtO_2$, catalytic hydrogenation using other efficient hydrogenation catalyst for the reduction of aliphatic nitro groups to their corresponding amines, reduction using iron metal in the presence of acid, reduction using iron metal/$FeCl_3$ in the presence of acid. In an embodiment, the hydrogenation catalyst may be recovered via filtration after the reaction is complete. In an embodiment, the hydrogenation catalyst may be recycled. In an embodiment, Formula I can be isolated via distillation. In an embodiment, Formula I can be purified via an extraction process and can optionally be further purified via distillation.

Example 3: Preparation of Formula I from Ethanolamine and Formaldehyde with Excess Acid Ethanolamine is an inexpensive feedstock chemical that is readily available in mass quantities. As discussed elsewhere herein, the direct reaction of formaldehyde with ethanolamine does not lead to the formation of Formula I. This is because of the increased reactivity of the amino group relative to the hydroxyl group. Suitably protected ethanolamine derivatives such as N-(2-hydroxyethyl)phthalimide can be used in place of ethanolamine to obtain Formula I in a two step sequence as in Scheme 2. In an embodiment, ethanolamine can be successfully reacted with formaldehyde (which can be employed in solid form as paraformaldehyde or trioxane) to obtain Formula I, provided that the reaction is carried out in an excess of acid (i.e., the molar equivalence of acid:ethanolamine is greater than 1). In an embodiment, when the reaction of ethanolamine with formaldehyde is carried out in the presence of an excess of strong acid, the reactive lone pair of the nitrogen group in ethanolamine is predominately in the protonated form, effectively inhibiting its ability to react with the aldehyde. In this way, the hydroxyl group of ethanolamine is then able to react with the aldehyde. Thus, two equivalents of the protonated form of ethanolamine can react with formaldehyde to yield Formula VII, which is the doubly protonated salt of I.

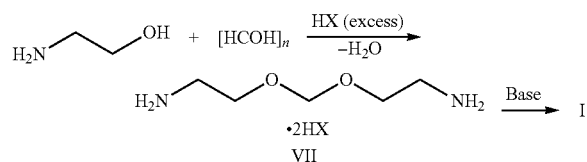

In an embodiment, deprotonation of Formula VII with a base then provides Formula I. In a preferred embodiment, ethanolamine is treated with acid prior to the addition of the formaldehyde species. Non-limiting examples of suitable acids include inorganic acids such as HCl and $H_2SO_4$, or organic acids such as p-toluenesulfonic acid or methanesulfonic acid. In an embodiment, formation of VII can be greatly facilitated by conditions that remove the formed water during the reaction. In an embodiment, removal of formed water can be accomplished by the addition of drying agents such as $MgSO_4$ to the reaction mixture. In another embodiment, removal of the water is effected via use of Dean-Stark type conditions. The reaction temperature can be in the range from 0° C. to 220° C. In an embodiment, ethanolamine hydrochloride is commercially available and it can be used in lieu of the in situ protonation of ethanolamine. Ethanolamine hydrochloride is a low melting solid and it can be reacted with paraformaldehyde (or trioxane) in the melt, and water removed via distillation. In an embodiment, conversion of Formula VII to Formula I can be accomplished by removal of any volatiles and by treatment with a base. In an embodiment, Formula I may be further purified via extraction techniques or by distillation.

Example 4: Preparation of Formula I from Ethanolamine and an Acetal of Formaldehyde with Excess Acid The embodiments of this example follow those of Example 3 with the substitution of an acetal of formaldehyde (Formula VII) used in place of formaldehyde. Non-limiting examples of suitable acetals include Formula VII; wherein R=alkyl or substituted alkyl group.

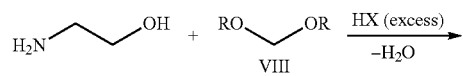

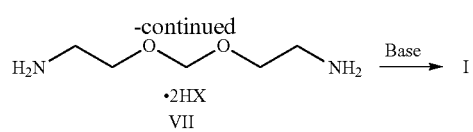

Example 5: Preparation of Formula X Via Catalytic Hydrogenation of the Formal of Ethylene Cyanohydrin (Formula XI)

The key embodiment of this example is the formation of Formula X via catalytic hydrogenation of the formal of ethylene cyanohydrin (Formula XI).

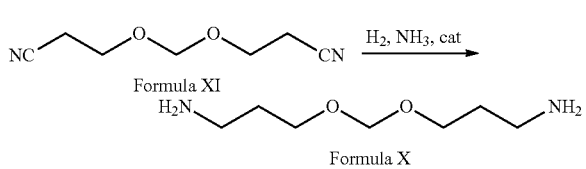

The starting compound Formula XI for this transformation can be prepared from the reaction of 2 molar equivalents of acrylonitrile with 1 molar equivalents of paraformaldehyde under aqueous reaction conditions according to the procedure detailed in U.S. Pat. No. 2,353,671. The key reaction of this disclosure is the transformation of the dinitrile Formula XI to the diamine Formula X. In an embodiment, this transformation may be accomplished using standard reaction protocols used for the reduction of aliphatic nitrile compounds to their corresponding amines in the art. In an embodiment, the transformation is carried out via a catalytic hydrogenation reaction. In an embodiment, the conversion of Formula X to Formula XI may be effected in the liquid phase employing a suitable active hydrogenation catalyst. In an embodiment, conventional hydrogenation catalysts include as the active component a noble metal from the group Ru, Rh, Pd, and Pt, or a transition metal the group Cu, Cr, Co, Ni, Fe, including, but not limited to, Raney catalysts and chromite catalyst. In an embodiment, bimetallic catalysts of one or more transition metals and/or noble metals may also be used. One of skill in the art, when viewing the present disclosure, will understand how to select a catalyst, including considerations of the useful life of any particular catalyst. In an embodiment, an example of a preferred catalyst is Raney Ni. In an embodiment, the hydrogenation can be conducted in the liquid or vapor phase at temperatures ranging between 20° C. and 200° C. and at pressures of 1 and 1000 atmospheres, and in another embodiment, in the temperate range between 60° C. and 150° C. and under pressures between 10 and 110 atmospheres. In an embodiment, the conversion of Formula X to Formula XI may be enhanced by the presence of ammonia during the reaction. In an embodiment, from 1 to 20 moles of ammonia per mole of Formula X is used. In an embodiment, hydrogenation of Formula XI can be carried out using anhydrous ammonia. In an embodiment, hydrogenation is carried out in aqueous ammonia, or in a suitable solvent such as, but not limited to, for example, methanol, ethanol, dioxane, or any solvent that is not substantially hydrogenated during the reaction or decomposed by the added ammonia. Upon the completion of the reaction, the catalyst can be removed via filtration and Formula X can be obtained after removal of any solvents. In an embodiment, Formula X can be further purified via distillation under reduced pressure.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A process for preparing a compound represented by Formula (1) from a compound of Formula (2):

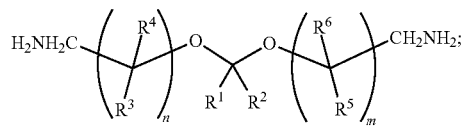

Formula (1)

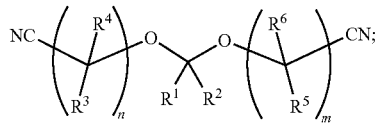

Formula (2)

wherein:
each of $R^1$ and $R^2$ is independently selected from the group consisting of hydrogen, alkyl group, cycloalkyl group and aromatic group; or both of $R^1$ and $R^2$ forms a cyclic radical;
each of $R^3$, $R^4$, $R^5$, and $R^6$ is independently selected from the group consisting of hydrogen, alkyl group, cycloalkyl group and aromatic group;
$R^3$ and $R^4$ can combine with each other to form a cyclic radical;
$R^5$ and $R^6$ can combine with each other to form a cyclic radical; and
each m and n is independently an integer ranging from 1 to 3; the process comprising reducing the compound of Formula (2) with a reducing agent to produce the compound of Formula (1) at a temperature of from about 15° C. to about 200° C.

2. The process of claim 1, wherein the reducing agent comprises molecular hydrogen.

3. The process according to claim 1, wherein the catalyst is recycled.

4. The process of claim 1, wherein the reduction is carried out in the presence of a metal-containing catalyst.

5. The process of claim 1, wherein the reduction is carried out in the presence of a catalyst and a catalyst promoter.

6. The process of claim 2, wherein the reduction is carried out at molecular hydrogen pressure of from about 80 psi to about 3000 psi.

7. The process of claim 1, wherein the reduction is carried out in the presence of ammonia.

8. The process of claim 1, wherein the reduction is carried out in the presence of anhydrous ammonia.

9. The process of claim 1, wherein the reduction is carried out in the presence of aqueous ammonia.

10. The process of claim 7, wherein the ammonia is recycled ammonia.

11. The process of claim 1, wherein the reduction is carried out in the presence of ammonia, the ammonia being present in an amount of from about 1 mole to about 40 moles per mole of the compound of Formula (2) used.

12. The process of claim 1, wherein the reduction is carried out in the presence of a solvent.

13. The process according to claim 1, wherein the reduction is carried out in a batch reactor.

14. The process according to claim 1, wherein the reduction is carried out in a continuous reactor.

15. The process according to claim 14, wherein the continuous reactor is selected from the group consisting of a flow reactor, a continuous stirred tank reactor, a trickle bed reactor, a loop reactor, a bubble reactor, a tube reactor, a pipe reactor, and a slurry reactor.

16. The process according to claim 1, wherein the compound of Formula (2) is selected from the group consisting of:

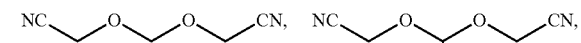
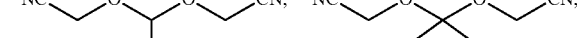
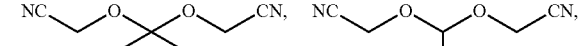
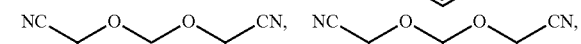
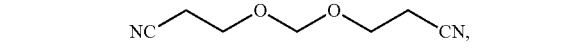

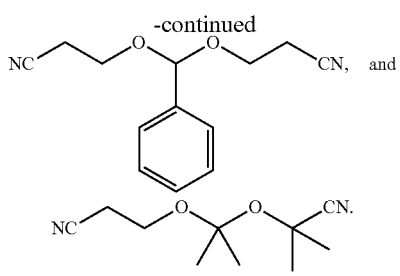

17. The process according to claim 1, wherein the compound of Formula (1) is selected from the group consisting of:

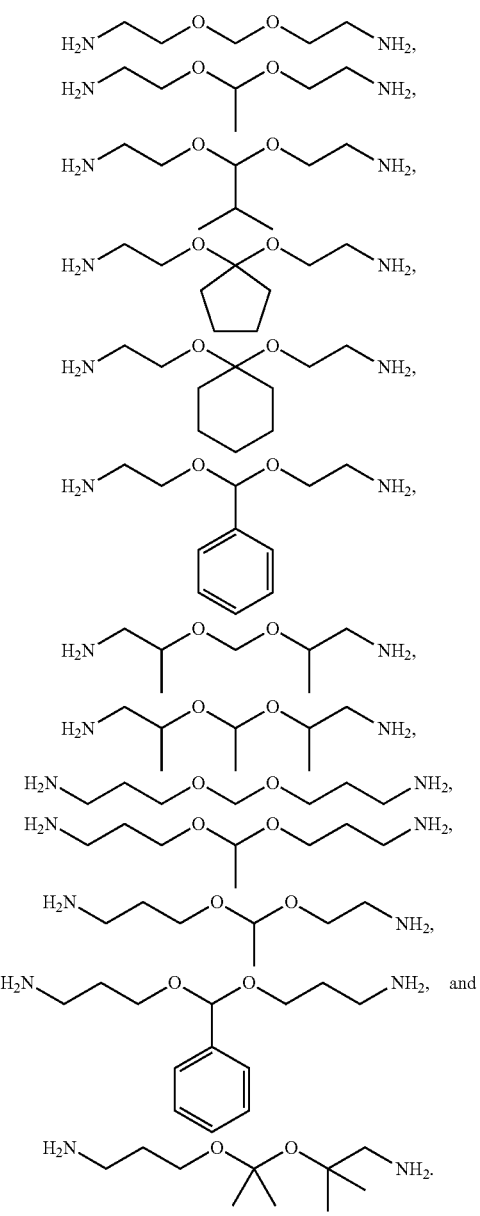

18. The process according to claim 1, wherein each m and n is independently 1 or 2.

19. The process according to claim 1, wherein m and n are 1.

20. The process according to claim 1, wherein m and n are 2.

21. The process according to claim 1, wherein each of $R^3$, $R^4$, $R^5$, and $R^6$ is independently selected from the group consisting of hydrogen, alkyl group, cycloalkyl group and aromatic group.

22. The process according to claim 1, wherein each of $R^3$, $R^4$, $R^5$, and $R^6$ is independently selected from the group consisting of hydrogen and alkyl group.

23. The process according to claim 1, wherein each of $R^3$, $R^4$, $R^5$, and $R^6$ is independently selected from the group consisting of hydrogen and methyl group.

24. The process according to claim 1, wherein each m and n is 1 or 2; and each of $R^3$, $R^4$, $R^5$, and $R^6$ is independently selected from the group consisting of hydrogen and alkyl group.

25. The process according to claim 1, wherein each of $R^1$ and $R^2$ is independently selected from the group consisting of hydrogen, alkyl group, cycloalkyl group and aromatic group.

26. The process according to claim 1, wherein each of $R^1$ and $R^2$ is independently selected from the group consisting of hydrogen and alkyl group.

27. The process according to claim 1, wherein $R^1$ and $R^2$ are both hydrogen.

28. The process according to claim 1, wherein $R^1$ is hydrogen and $R^2$ is alkyl group.

29. The process according to claim 1, wherein $R^1$ is hydrogen and $R^2$ is methyl.

30. The process according to claim 1, wherein $R^1$ and $R^2$ are both alkyl group.

31. The process according to claim 1, wherein $R^1$ and $R^2$ are both methyl.

32. The process according to claim 1, wherein each of $R^1$, $R^2$, $R^3$, $R^4$, $R^5$, and $R^6$ is independently selected from the group consisting of hydrogen and alkyl group; and each m and n is independently an integer ranging from 1 to 3.

33. The process according to claim 32, wherein each m and n is independently 1 or 2.

34. The process according to claim 32, wherein m and n are 1.

35. The process according to claim 32, wherein m and n are 2.

36. The process according to claim 32, wherein each of $R^1$, $R^2$, $R^3$, $R^4$, $R^5$, and $R^6$ is independently selected from the group consisting of hydrogen and methyl.

37. A process for preparing the compound represented by Formula I,

Formula I

H₂N~~~O~~O~~~NH₂ the process comprising a first step, wherein the first step is a process for preparing the compound represented by Formula VII Formula VII

H₂N~~~O~~O~~~NH₂ · HX;

wherein HX indicates that the compound represented by Formula VII is a doubly protonated salt of the compound represented by Formula I;

said first step comprising reacting ethanolamine with formaldehyde or paraformaldehyde in the presence of an acid to produce the compound represented by Formula VII or reacting ethanolamine hydrochloride with paraformaldehyde or trioxane to produce the compound represented by Formula VII;

and a second step, wherein the second step is a process for preparing the compound represented by Formula I from the compound represented by Formula VII, said second step comprising reacting Formula VII with a base to produce the compound represented by Formula I.

38. A process for preparing the compound represented by Formula VII,

Formula VII

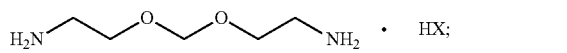

wherein HX indicates that the compound represented by Formula VII is a doubly protonated salt;

the process comprising reacting ethanolamine with formaldehyde or paraformaldehyde in the presence of an acid to produce the compound represented by Formula VII or reacting ethanolamine hydrochloride with paraformaldehyde or trioxane to produce the compound represented by Formula VII.

39. The process of claim 37, wherein the molar equivalence of acid:ethanolamine is greater than 1.

40. The process of claim 37, wherein ethanolamine is combined with acid prior to the addition of formaldehyde or paraformaldehyde.

41. The process of claim 37, wherein the acid is an inorganic acid.

42. The process of claim 41, wherein the acid is HCl or $H_2SO_4$.

43. The process of claim 37, wherein the reaction temperature of the first step is in the range from about 0° C. to about 220° C.

44. The process of claim 37, wherein a drying agent is a component of the reaction mixture of the first step.

45. The process of claim 37, wherein water is removed from the reaction using a Dean-Stark apparatus in the first step.

46. The process of claim 37, wherein the compound represented by Formula I is purified by extraction techniques or distillation.

47. The process of claim 38, wherein the molar equivalence of acid:ethanolamine is greater than 1.

48. The process of claim 38, wherein ethanolamine is combined with acid prior to the addition of formaldehyde or paraformaldehyde.

49. The process of claim 38, wherein the acid is an inorganic acid.

50. The process of claim 49, wherein the acid is HCl or $H_2SO_4$.

51. The process of claim 37, wherein the acid is an organic acid.

52. The process of claim 51, wherein the acid is p-toluenesulfonic acid or methanesulfonic acid.

53. The process of claim 38, wherein the acid is an organic acid.

54. The process of claim 53, wherein the acid is p-toluenesulfonic acid or methanesulfonic acid.

* * * * *